United States Patent
Aebi et al.

(10) Patent No.: US 9,505,742 B2
(45) Date of Patent: Nov. 29, 2016

(54) 3,4-DIHYDRO-2H-ISOQUINOLINE-1-ONE AND 2,3-DIHYDRO-ISOINDOL-1-ONE COMPOUNDS

(71) Applicant: Hoffmann-La Roche Inc., Little Falls, NJ (US)

(72) Inventors: Johannes Aebi, Binningen (CH); Kurt Amrein, Itingen (CH); Wenming Chen, Shanghai (CN); Benoit Hornsperger, Altkirch (FR); Bernd Kuhn, Reinach BL (CH); Dongbo Li, Shanghai (CN); Yongfu Liu, Shanghai (CN); Hans P. Maerki, Basel (CH); Rainer E. Martin, Basel (CH); Alexander Mayweg, Basel (CH); Xuefei Tan, Shanghai (CN); Lisha Wang, Basel (CH); Jun Wu, Shanghai (CN); Mingwei Zhou, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/947,730

(22) Filed: Nov. 20, 2015

(65) Prior Publication Data
US 2016/0075686 A1    Mar. 17, 2016

Related U.S. Application Data

(63) Continuation of application No. PCT/EP2014/060784, filed on May 26, 2014.

(30) Foreign Application Priority Data

May 27, 2013    (CN) .................. PCT/CN2013/076276

(51) Int. Cl.
C07D 401/14    (2006.01)
A61K 31/437    (2006.01)
C07D 471/04    (2006.01)

(52) U.S. Cl.
CPC ........... *C07D 401/14* (2013.01); *C07D 471/04* (2013.01)

(58) Field of Classification Search
None
See application file for complete search history.

(56) References Cited

U.S. PATENT DOCUMENTS

2011/0118241 A1    5/2011    Hartmann et al.

FOREIGN PATENT DOCUMENTS

| WO | 2012/035078 A1 | 3/2012 |
| WO | 2013/079452 A1 | 6/2013 |

OTHER PUBLICATIONS

Written Opinion for International Patent Application No. PCT/EP2014/060784, 7 pages, (2014).

*Primary Examiner* — Zinna Northington Davis

(57) ABSTRACT

The invention provides novel compounds having the general formula (I)

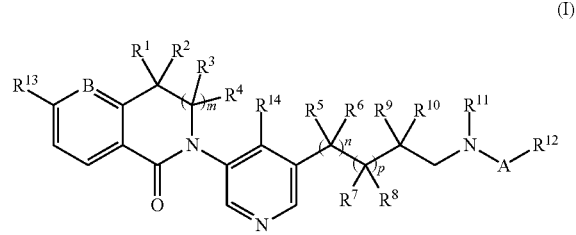

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, A, B, m, n and p are as described herein, compositions including the compounds and methods of using the compounds.

24 Claims, No Drawings

3,4-DIHYDRO-2H-ISOQUINOLINE-1-ONE AND 2,3-DIHYDRO-ISOINDOL-1-ONE COMPOUNDS

The present invention relates to organic compounds useful for therapy or prophylaxis in a mammal, and in particular to aldosterone synthase inhibitors for the treatment or prophylaxis of chronic kidney disease, congestive heart failure, hypertension, primary aldosteronism and Cushing syndrome.

The present invention provides novel compounds of formula (I)

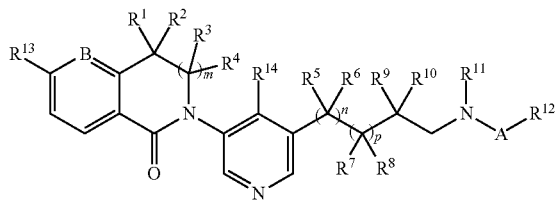

wherein
$R^1$, $R^2$, $R^3$ and $R^4$ are independently selected from H, alkyl and cycloalkyl;
$R^5$, $R^6$, $R^7$ and $R^9$ are independently selected from H, alkyl, halogen and hydroxy;
$R^8$ and $R^{11}$ together form —$CH_2$—$CH_2$—;
$R^{10}$ is H or $R^{10}$ and $R^{11}$ together form —$(CH_2)_w$—;
A is —C(O)— or —S(O)$_2$—;
B is —C— or —N—;
$R^{12}$ is alkyl, cycloalkyl or substituted heteroaryl, wherein substituted heteroaryl is substituted with one to three substituent independently selected from H, alkyl, cycloalkyl, hydroxy, alkoxy, cyano and halogen;
$R^{13}$ is halogen, cyano, alkoxy or haloalkoxy;
$R^{14}$ is H, alkyl or halogen;
m, n and p are independently selected from zero and 1;
w is 1, 2 or 3;
with the proviso that 2-[5-(1-acetyl-pyrrolidin-3-yl)-pyridin-3-yl]-5-chloro-3,3-dimethyl-2,3-dihydro-isoindol-1-one and 2-(1'-acetyl-1',2',3',4',5',6'-hexahydro-[3,4'] bipyridinyl-5-yl)-5-chloro-3,3-dimethyl-2,3-dihydro-isoindol-1-one are excluded;
and pharmaceutically acceptable salts thereof.

Herein we describe inhibitors of aldosterone synthase that have the potential to protect from organ/tissue damage caused by an absolute or relative excess of aldosterone. Hypertension affects about 20% of the adult population in developed countries. In persons 60 years and older, this percentage increases to above 60%. Hypertensive subjects display an increased risk of other physiological complications including stroke, myocardial infarction, atrial fibrillation, heart failure, peripheral vascular disease and renal impairment. The renin angiotensin aldosterone system is a pathway that has been linked to hypertension, volume and salt balance and more recently to contribute directly to end organ damage in advanced stages of heart failure or kidney disease. ACE inhibitors and angiotensin receptor blockers (ARBs) are successfully used to improve duration and quality of life of patients. These drugs are not yielding maximum protection. In a relatively large number of patients ACE and ARB's lead to so-called aldosterone breakthrough, a phenomenon where aldosterone levels, after a first initial decline, return to pathological levels. It has been demonstrated that the deleterious consequences of inappropriately increased aldosterone levels (in relation to salt intake/levels) can be minimized by aldosterone blockade with mineralocorticoid receptor antagonists. A direct inhibition of aldosterone synthesis is expected to provide even better protection as it will also reduce non-genomic effects of aldosterone as well.

The effects of aldosterone on Na/K transport lead to increased re-absorption of sodium and water and the secretion of potassium in the kidneys. Overall this results in increased blood volume and, therefore, increased blood pressure. Beyond its role in the regulation of renal sodium re-absorption aldosterone can exert deleterious effects on the kidney, the heart and the vascular system especially in a "high sodium" context. It has been shown that under such conditions aldosterone leads to increased oxidative stress which ultimately may contribute to organ damage. Infusion of aldosterone into renally compromised rats (either by high salt treatment or by unilaterally nephrectomy) induces a wide array of injuries to the kidney including glomerular expansion, podocyte injury, interstitial inflammation, mesangial cell proliferation and fibrosis reflected by proteinuria. More specifically aldosterone was shown to increase the expression of the adhesion molecule ICAM-1 in the kidney. ICAM-1 is critically involved in glomerular inflammation. Similarly, aldosterone was shown to increase the expression of inflammatory cytokines, such as interleukin IL-1b and IL-6, MCP-1 and osteopontin. On a cellular level it was demonstrated that in vascular fibroblasts aldosterone increased the expression of type I collagen mRNA, a mediator of fibrosis. Aldosterone also stimulates type IV collagen accumulation in rat mesangial cells and induces plasminogen activator inhibitor-1 (PAI-1) expression in smooth muscle cells. In summary aldosterone has emerged as a key hormone involved in renal damage. Aldosterone plays an equally important role in mediating cardiovascular risk.

There is ample preclinical evidence that MR-antagonists (spironolactone and eplerenone) improve blood pressure, cardiac and renal function in various preclinical models.

More recently preclinical studies highlight the important contribution of CYP11B2 to cardiovascular and renal morbidity and mortality. The CYP11B2 inhibitor FAD286 and the MR antagonist spironolactone were evaluated in a rat model of chronic kidney disease (high angiotensin II exposure; high salt and uni-nephrectomy). Angiotensin II and high salt treatment caused albuminuria, azotemia, renovascular hypertrophy, glomerular injury, increased PAI-1, and osteopontin mRNA expression, as well as tubulointerstitial fibrosis. Both drugs prevented these renal effects and attenuated cardiac and aortic medial hypertrophy. Following 4 weeks of treatment with FAD286, plasma aldosterone was reduced, whereas spironolactone increased aldosterone at 4 and 8 weeks of treatment. Similarly only spironolactone but not FAD286 enhanced angiotensin II and salt-stimulated PAI-1 mRNA expression in the aorta and the heart. In other studies the CYP11B2 inhibitor FAD286 improved blood pressure and cardiovascular function and structure in rats with experimental heart failure. In the same studies FAD286 was shown to improve kidney function and morphology.

Administration of an orally active CYP11B2 inhibitor, LCI699, to patients with primary aldosteronism, lead to the conclusion that it effectively inhibits CYP11B2 in patients with primary aldosteronism resulting in significantly lower circulating aldosterone levels and that it corrected the hypokalemia and mildly decreased blood pressure. The effects on the glucocorticoid axis were consistent with a poor selectivity of the compound and a latent inhibition of cortisol synthesis. Taken together these data support the concept that a CYP11B2 inhibitor can lower inappropriately high aldosterone levels. Achieving good selectivity against CYP11B1 is important to be free of undesired side effects on the HPA axis and will differentiate different CYP11B2 inhibitors.

The compounds of the present invention according formula (I) are potent inhibitors of CYPB11B2 and present an improved selectivity towards CYP11B2 versus CYP11B1 combined with an improved metabolic stability.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of chronic kidney disease, congestive heart failure, hypertension, primary aldosteronism and Cushing syndrom and the use of the said compounds, salts or esters for the production of medicaments for the treatment or prophylaxis of chronic kidney disease, congestive heart failure, hypertension, primary aldosteronism and Cushing syndrom.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl and isopropyl, n-butyl, iso-butyl, sec-butyl, and. Particular alkyl groups include methyl, ethyl, propyl and isopropyl. More particular alkyl groups are methyl and ethyl.

The term "cycloalkyl" denotes a monovalent saturated monocyclic hydrocarbon group of 3 to 10 ring carbon atoms. In particular embodiments, cycloalkyl denotes a monovalent saturated monocyclic hydrocarbon group of 3 to 8 ring carbon atoms. Examples for cycloalkyl are cyclopropyl, cyclobutanyl, cyclopentyl, cyclohexyl or cycloheptyl. Particular cycloalkyl group is cyclopropyl.

The term "halogen" and "halo" are used interchangeably herein and denote fluoro, chloro, bromo, or iodo. Particular halogens are chloro and fluoro. Particular halogen is chloro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl and quinoxalinyl. Particular heteroaryl group is pyridinyl. Also particular heteroaryl groups are imidazolyl, isoxazolyl, oxazolyl, pyrazolyl and pyrimidinyl. Further particular heteroaryl groups are pyridinyl and pyrazolyl.

The term "hydroxy" denotes a —OH group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. µAdditionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the tert-butoxycarbonyl (Boc).

The abbreviation uM means microMolar and is equivalent to the symbol µM.

The compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^2H$ ("D"), $^3H$ ("T"), $^{11}C$, $^{13}C$, $^{14}C$, $^{13}N$, $^{15}N$, $^{15}O$, $^{17}O$, $^{32}P$, $^{33}P$, $^{35}S$, $^{18}F$, $^{36}Cl$, $^{123}I$ and $^{125}I$.

Certain isotopically labeled compounds of the present invention (e.g., those labeled with $^{3}H$ or $^{14}C$) are useful in compound and/or substrate tissue distribution assays. Tritiated ($^{3}H$) and carbon-14 ($^{14}C$) isotopes are useful for their ease of preparation and detectability. Further substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present inventions can generally be prepared by following procedures analogous to those disclosed in the Schemes and/or in the Examples herein below, by substituting a non-isotopically labeled reagent with a isotopically labeled reagent. In particular, compounds of formula (I) wherein one or more H atom have been replaced by a $^{2}H$ atom are also an embodiment of this invention.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

The present invention also relates to compounds according to formüa (I) as described herein, wherein (I)

wherein
$R^1$, $R^2$, $R^3$ and $R^4$ are independently selected from H, alkyl and cycloalkyl;
$R^5$, $R^6$, $R^7$ and $R^9$ are independently selected from H, alkyl, halogen and hydroxy;
$R^8$ and $R^{11}$ together form —$CH_2$—$CH_2$—;
$R^{10}$ is H or $R^{10}$ and $R^{11}$ together form —$(CH_2)_w$—;
A is —C(O)— or —$S(O)_2$—;
$R^{12}$ is alkyl, cycloalkyl or substituted heteroaryl, wherein substituted heteroaryl is substituted with one to three subtituent independently selected from H, alkyl and halogen;
$R^3$ is halogen;
$R^{14}$ is H, alkyl or halogen;
m, n and p are independently selected from zero and 1;
w is 1, 2 or 3;

with the proviso that 2-[5-(1-acetyl-pyrrolidin-3-yl)-pyridin-3-yl]-5-chloro-3,3-dimethyl-2,3-dihydro-isoindol-1-one and 2-(1'-acetyl-1',2',3',4',5',6'-hexahydro-[3,4'] bipyridinyl-5-yl)-5-chloro-3,3-dimethyl-2,3-dihydro-isoindol-1-one are excluded;
and pharmaceutically acceptable salts thereof.

Also an embodiment of the present invention are compounds according to formula (I) as described herein wherein $R^1$ and $R^2$ are independently selected from H and alkyl.

A particular embodiment of the present invention are compounds according to formula (I) as described herein, wherein $R^1$ and $R^2$ are alkyl.

A further particular embodiment of the present invention are compounds according to formula (I) as described herein, wherein $R^1$ and $R^2$ are methyl.

In a further embodiment of the present invention are compounds according to formula (I) as described herein, wherein m and n is zero.

Another further embodiment of the present invention are compounds according to formula (I) as described herein, wherein p is 1.

Another embodiment of the present invention are compounds according to formula (I) as described herein, wherein $R^7$ is H or halogen.

Another particular embodiment of the present invention are compounds according to formula (I) as described herein, wherein $R^7$ is H or fluoro.

A more particular embodiment of the present invention are compounds according to formula (I) as described herein, wherein $R^7$ is H.

A particular embodiment of the present invention are compounds according to formula (I) as described herein, wherein $R^9$ is H.

Another particular embodiment of the present invention are compounds according to formula (I) as described herein, wherein $R^{10}$ is H.

Also a particular embodiment of the present invention are compounds according to formula (I) as described herein, wherein A is —$S(O)_2$—.

Also a particular embodiment of the present invention are compounds according to formula (I) as described herein, wherein B is —C—.

Another embodiment of the present invention are compounds according to formula (I) as described herein, wherein $R^{12}$ is alkyl or cycloalkyl.

Another particular embodiment of the present invention are compounds according to formula (I) as described herein, wherein $R^{12}$ is alkyl.

A further particular embodiment of the present invention are compounds according to formula (I) as described herein, wherein $R^2$ is ethyl, propyl, isopropyl.

A more particular embodiment of the present invention are compounds according to formula (I) as described herein, wherein $R^{12}$ is ethyl.

Also an embodiment of the present invention are compounds according to formula (I) as described herein, wherein $R^{13}$ is cyano or halogen.

Also an embodiment of the present invention are compounds according to formula (I) as described herein, wherein $R^{13}$ is chloro. A further particular embodiment of the present invention are compounds according to formula (I) as described herein, wherein $R^{14}$ is H.

A particular embodiment of the present invention are compounds according to formula (I) as described herein, wherein $R^1$ and $R^2$ are methyl, $R^7$, $R^9$, $R^{10}$ and $R^{14}$ are H, $R^{13}$ is chloro, A is —$S(O)_2$—, m and n are zero, p is 1 and $R^{12}$ is alkyl or cycloalkyl.

A more particular embodiment of the present invention are compounds according to formula (I) as described herein, wherein $R^1$ and $R^2$ are methyl, $R^7$, $R^9$, $R^{10}$ and $R^{14}$ are H, $R^{13}$ is chloro, A is —S(O)$_2$—, m and n are zero, p is 1 and $R^{12}$ is alkyl.

Particular examples of compounds of formula (I) as described herein are selected from 5-Chloro-3,3-dimethyl-2-[5-(1-propanoylpiperidin-4-yl)pyridin-3-yl]isoindol-1-one;

5-Chloro-2-[5-(1-ethylsulfonylpiperidin-4-yl)pyridin-3-yl]-3,3-dimethylisoindol-1-one;

5-Chloro-3,3-dimethyl-2-[5-(1-methylsulfonylpiperidin-4-yl)pyridin-3-yl]isoindol-1-one;

5-Chloro-2-[5-(1-ethylsulfonylpiperidin-3-yl)pyridin-3-yl]-3,3-dimethylisoindol-1-one;

5-Chloro-3,3-dimethyl-2-[5-[(3R or 3S)-1-methylsulfonylpiperidin-3-yl]pyridin-3-yl]isoindol-1-one;

5-Chloro-3,3-dimethyl-2-[5-[(3S or 3R)-1-methylsulfonylpiperidin-3-yl]pyridin-3-yl]isoindol-1-one;

5-Chloro-2-[5-(1-ethylsulfonylpyrrolidin-3-yl)pyridin-3-yl]-3,3-dimethylisoindol-1-one;

5-Chloro-3,3-dimethyl-2-[5-[(3R or 3S)-1-propylsulfonylpyrrolidin-3-yl]pyridin-3-yl]isoindol-1-one;

5-Chloro-3,3-dimethyl-2-[5-[(3S or 3R)-1-propylsulfonylpyrrolidin-3-yl]pyridin-3-yl]isoindol-1-one;

5-Chloro-3,3-dimethyl-2-[5-[(3R or 3S)-1-propan-2-ylsulfonylpyrrolidin-3-yl]pyridin-3-yl]isoindol-1-one;

5-Chloro-3,3-dimethyl-2-[5-[(3S or 3R)-1-propan-2-ylsulfonylpyrrolidin-3-yl]pyridin-3-yl]isoindol-1-one;

5-Chloro-2-[5-[(3R or 3S)-1-cyclopropylsulfonylpyrrolidin-3-yl]pyridin-3-yl]-3,3-dimethylisoindol-1-one;

5-Chloro-2-[5-[(3S or 3R)-1-cyclopropylsulfonylpyrrolidin-3-yl]pyridin-3-yl]-3,3-dimethylisoindol-1-one;

5-Chloro-2-[5-(3-fluoro-1-propan-2-ylsulfonylpyrrolidin-3-yl)pyridin-3-yl]-3,3-dimethylisoindol-1-one;

5-Chloro-3,3-dimethyl-2-[5-(1-propylsulfonylpiperidin-4-yl)pyridin-3-yl]isoindol-1-one;

5-Chloro-3,3-dimethyl-2-[5-(1-propan-2-ylsulfonylpiperidin-4-yl)pyridin-3-yl]isoindol-1-one;

5-Chloro-2-[5-(1-cyclopropylsulfonylpiperidin-4-yl)pyridin-3-yl]-3,3-dimethylisoindol-1-one;

5-Chloro-3,3-dimethyl-2-[5-[1-(4-methylpyridine-3-carbonyl)piperidin-4-yl]pyridin-3-yl]isoindol-1-one;

5-Chloro-2-[5-[1-(3-chloropyridine-4-carbonyl)piperidin-4-yl]pyridin-3-yl]-3,3-dimethylisoindol-1-one;

5-Chloro-2-[5-[1-(3-chloropyridine-2-carbonyl)piperidin-4-yl]pyridin-3-yl]-3,3-dimethylisoindol-1-one;

5-Chloro-2-[5-(1-ethylsulfonylpiperidin-4-yl)pyridin-3-yl]-3H-isoindol-1-one;

5-Chloro-2-[5-(1-propan-2-ylsulfonylpiperidin-4-yl)pyridin-3-yl]-3H-isoindol-1-one;

5-Chloro-2-[5-[1-(4-methylpyridine-3-carbonyl)piperidin-4-yl]pyridin-3-yl]-3H-isoindol-1-one;

(3R or 3S)-5-Chloro-2-[5-(1-ethylsulfonylpiperidin-4-yl)pyridin-3-yl]-3-methyl-3H-isoindol-1-one;

(3S or 3R)-5-Chloro-2-[5-(1-ethylsulfonylpiperidin-4-yl)pyridin-3-yl]-3-methyl-3H-isoindol-1-one;

(3R or 3S)-5-Chloro-3-methyl-2-[5-(1-propan-2-ylsulfonylpiperidin-4-yl)pyridin-3-yl]-3H-isoindol-1-one;

(3S or 3R)-5-Chloro-3-methyl-2-[5-(1-propan-2-ylsulfonylpiperidin-4-yl)pyridin-3-yl]-3H-isoindol-1-one;

(3R or 3S)-5-Chloro-3-methyl-2-[5-[1-(4-methylpyridine-3-carbonyl)piperidin-4-yl]pyridin-3-yl]-3H-isoindol-1-one;

(3S or 3R)-5-Chloro-3-methyl-2-[5-[1-(4-methylpyridine-3-carbonyl)piperidin-4-yl]pyridin-3-yl]-3H-isoindol-1-one;

5-Chloro-2-[5-(1-ethylsulfonyl-4-fluoropiperidin-4-yl)pyridin-3-yl]-3,3-dimethylisoindol-1-one;

5-Chloro-2-[5-(4-fluoro-1-propan-2-ylsulfonylpiperidin-4-yl)pyridin-3-yl]-3,3-dimethylisoindol-1-one;

5-Chloro-2-[5-(1-ethylsulfonylazetidin-3-yl)pyridin-3-yl]-3,3-dimethylisoindol-1-one;

2-[5-(1-Acetylazetidin-3-yl)pyridin-3-yl]-5-chloro-3,3-dimethylisoindol-1-one;

5-Chloro-3,3-dimethyl-2-[5-(1-propylsulfonylazetidin-3-yl)pyridin-3-yl]isoindol-1-one;

5-Chloro-2-[5-(1-cyclopropylsulfonylazetidin-3-yl)pyridin-3-yl]-3,3-dimethylisoindol-1-one;

5-Chloro-3,3-dimethyl-2-[5-[1-(4-methylpyridine-3-carbonyl)azetidin-3-yl]pyridin-3-yl]isoindol-1-one;

and pharmaceutically acceptable salts thereof.

Further particular examples of compounds of formula (I) as described herein are selected from 5-Chloro-2-[5-(1-ethylsulfonylpiperidin-4-yl)pyridin-3-yl]-3,3-dimethylisoindol-1-one;

5-Chloro-3,3-dimethyl-2-[5-(1-propylsulfonylpiperidin-4-yl)pyridin-3-yl]isoindol-1-one;

5-Chloro-3,3-dimethyl-2-[5-(1-propan-2-ylsulfonylpiperidin-4-yl)pyridin-3-yl]isoindol-1-one;

5-Chloro-2-[5-(1-cyclopropylsulfonylpiperidin-4-yl)pyridin-3-yl]-3,3-dimethylisoindol-1-one;

and pharmaceutically acceptable salts thereof.

Also particular examples of compounds of formula (I) as described herein are selected from 5-Chloro-2-[5-(4-fluoro-1-propylsulfonyl-4-piperidyl)-3-pyridyl]-3,3-dimethyl-isoindolin-1-one;

5-Chloro-2-[5-(1-cyclopropylsulfonyl-4-fluoro-4-piperidyl)-3-pyridyl]-3,3-dimethyl-isoindolin-1-one;

2-[5-(4-Fluoro-1-isopropylsulfonyl-4-piperidyl)-3-pyridyl]-3,3-dimethyl-1-oxo-isoindoline-5-carbonitrile;

6-[5-(1-Ethylsulfonyl-4-fluoro-4-piperidyl)-3-pyridyl]-2-methoxy-7,7-dimethyl-pyrrolo[3,4-b]pyridin-5-one;

6-[5-[4-Fluoro-1-(1-methylpyrazole-4-carbonyl)-4-piperidyl]-3-pyridyl]-2-methoxy-7,7-dimethyl-pyrrolo[3,4-b]pyridin-5-one;

6-[5-(4-Fluoro-1-isopropylsulfonyl-4-piperidyl)-3-pyridyl]-2-methoxy-7,7-dimethyl-pyrrolo[3,4-b]pyridin-5-one;

6-[5-(4-Fluoro-1-propylsulfonyl-4-piperidyl)-3-pyridyl]-2-methoxy-7,7-dimethyl-pyrrolo[3,4-b]pyridin-5-one;

6-[5-[4-Fluoro-1-(1-methylimidazole-2-carbonyl)-4-piperidyl]-3-pyridyl]-2-methoxy-7,7-dimethyl-pyrrolo[3,4-b]pyridin-5-one;

6-[5-(1-Cyclopropylsulfonyl-4-fluoro-4-piperidyl)-3-pyridyl]-2-methoxy-7,7-dimethyl-pyrrolo[3,4-b]pyridin-5-one;

6-[5-(1-Ethylsulfonyl-4-piperidyl)-3-pyridyl]-2-methoxy-7,7-dimethyl-pyrrolo[3,4-b]pyridin-5-one;

2-Methoxy-7,7-dimethyl-6-[5-[1-(1-methylpyrazole-4-carbonyl)-4-piperidyl]-3-pyridyl]pyrrolo[3,4-b]pyridin-5-one;

2-Methoxy-7,7-dimethyl-6-[5-[1-(2-methylpyrazole-3-carbonyl)-4-piperidyl]-3-pyridyl]pyrrolo[3,4-b]pyridin-5-one;

2-Methoxy-7,7-dimethyl-6-[5-[1-(4-methylpyridine-3-carbonyl)-4-piperidyl]-3-pyridyl]pyrrolo[3,4-b]pyridin-5-one;

and pharmaceutically acceptable salts thereof.

Also further particular examples of compounds of formula (I) as described herein are selected from (3S or 3R)-5-Chloro-3-methyl-2-[5-(1-propan-2-ylsulfonylpiperidin-4-yl)pyridin-3-yl]-3H-isoindol-1-one;

5-Chloro-2-[5-(1-ethylsulfonyl-4-fluoropiperidin-4-yl)pyridin-3-yl]-3,3-dimethylisoindol-1-one;

5-Chloro-2-[5-(4-fluoro-1-propan-2-ylsulfonylpiperidin-4-yl)pyridin-3-yl]-3,3-dimethylisoindol-1-one;
and pharmaceutically acceptable salts thereof.

Also further particular examples of compounds of formula (I) as described herein are selected from (3R or 3S)-5-Chloro-2-[5-(1-ethylsulfonylpiperidin-4-yl)pyridin-3-yl]-3-methyl-3H-isoindol-1-one
5-Chloro-2-[5-(1-cyclopropylsulfonyl-4-fluoro-4-piperidyl)-3-pyridyl]-3,3-dimethyl-isoindolin-1-one;
2-[5-(4-Fluoro-1-isopropylsulfonyl-4-piperidyl)-3-pyridyl]-3,3-dimethyl-1-oxo-isoindoline-5-carbonitrile;
and pharmaceutically acceptable salts thereof.

A more particular example of compounds of formula (I) as described herein is
5-Chloro-2-[5-(1-ethylsulfonylpiperidin-4-yl)pyridin-3-yl]-3,3-dimethylisoindol-1-one;
and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization. The substituents and indices used in the following description of the processes have the significance given herein.

The following abbreviations are used in the present text:
AcOH=acetic acid, BOC=t-butyloxycarbonyl, BuLi=butyllithium, CDI=1,1-carbonyldiimidazole, DCM=dichloromethane, DBU=2,3,4,6,7,8,9,10-octahydro-pyrimido[1,2-a]azepine, DCE=1,2-dichloroethane, DIBALH=di-i-butylaluminium hydride, DCC=N,N'-dicyclohexylcarbodiimide, DMA=N,N-dimethylacetamide, DMAP=4-dimethylaminopyridine, DMF=N,N-dimethylformamide, EDCI=N-(3-dimethylaminopropyl)-N'-ethylcarbodiimide hydrochloride, EtOAc=ethylacetate, EtOH=ethanol, Et$_2$O=diethylether, Et$_3$N=triethylamine, eq=equivalents, HATU=O-(7-azabenzotriazol-1-yl)-1,1,3,3-tetramethyluronium hexafluorophosphate, HPLC=high performance liquid chromatography, HOBT=1-hydroxybenzo-triazole, Huenig's base=iPr$_2$NEt=N-ethyl diisopropylamine, IPC=in process control, LAH=lithium aluminium hydride, LDA=lithium diisopropylamide, LiBH$_4$=lithium borohydride, MeOH=methanol, NaBH$_3$CN, sodium cyanoborohydride, NaBH$_4$=sodium borohydride, NaI=sodium iodide, Red-Al=sodium bis(2-methoxyethoxy) aluminium hydride, RT=room temperature, TBDMSCl=t-butyldimethylsilyl chloride, TFA=trifluoroacetic acid, THF=tetrahydrofuran, quant=quantitative.

Halogen or triflate, preferably iodo substituted pyridine compounds 2 react with aryl lactams 1 in solvents like 1,4-dioxane, in the presence of copper (I) iodide, potassium or cesium carbonate, a chelating 1,2-diamino compound like N,N'-dimethylethylenediamine or trans-1,2-diamino-cyclohexane or a chelating beta keto ester compound like 2-isobutyryl-cyclohexanone, at elevated temperatures, preferable with the aid of microwave heating to form lactam substituted heterocyclic compounds 3 as described in Scheme 1a (step a). Compounds 3 can be transformed into compounds 8 by i) Suzuki reactions with alkenyl boronates 4, 5, 6 or 7 (compounds which are known or can be readily prepared by methods known in the art) e.g. in the presence of catalysts, such as tri-o-tolylphosphine/palladium(II)acetate, tetrakis-(triphenylphosphine)-palladium, bis(triphenylphosphine) palladium(II)chloride or dichloro[1,1'-bis(diphenylphosphino)-ferrocene]palladium(II) optionally in the form of a dichloromethane complex (1:1), and in the presence of a base, such as aqueous or non aqueous potassium phosphate, cesium, sodium or potassium carbonate, in a solvent, such as dimethylsulfoxide, toluene, ethanol, dioxane, tetrahydrofuran or N,N-dimethylformamide, and in an inert atmosphere such as argon or nitrogen, in a temperature range preferably between room temperature and about 130° C.; ii) catalytic hydrogenation (step b, c). Compounds 8 with R$^{103}$ being a protecting group can then be converted into compounds 9 by removal of the protecting group R$^{103}$ and reaction with a suitable activated carboxyl or sulfonyl compound (steps d, e). Alternatively, alkenyl boronates 4, 5, 6 or 7 can be reacted with amino-pyridines 10 under conditions as described for the reaction between compounds 3 and alkenyl boronates 4, 5, 6 or 7 in Scheme 1a leading to amino-pyridine compounds 11 (Scheme 1b, steps b, c). Amino-pyridine compounds 11 can then be converted into the corresponding halo compounds 12 e.g. by using t-BuNO$_2$, CuBr$_2$ or potassium iodide, sodium nitrite, p-toluene sulfonic acid in a solvent like acetonitrile, methanol or ethanol at temperatures between 0° C. and the reflux temperature of the solvents (Scheme 1b, steps f). Transformation of halo compounds 12 into compounds 9 (Scheme 1c) is then being performed as described in Scheme 1a.

Scheme 1a

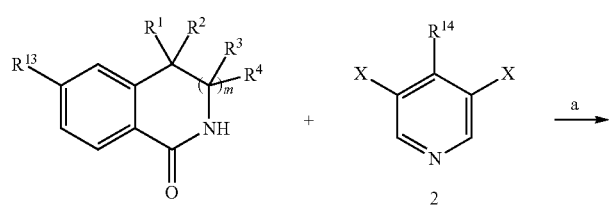

-continued
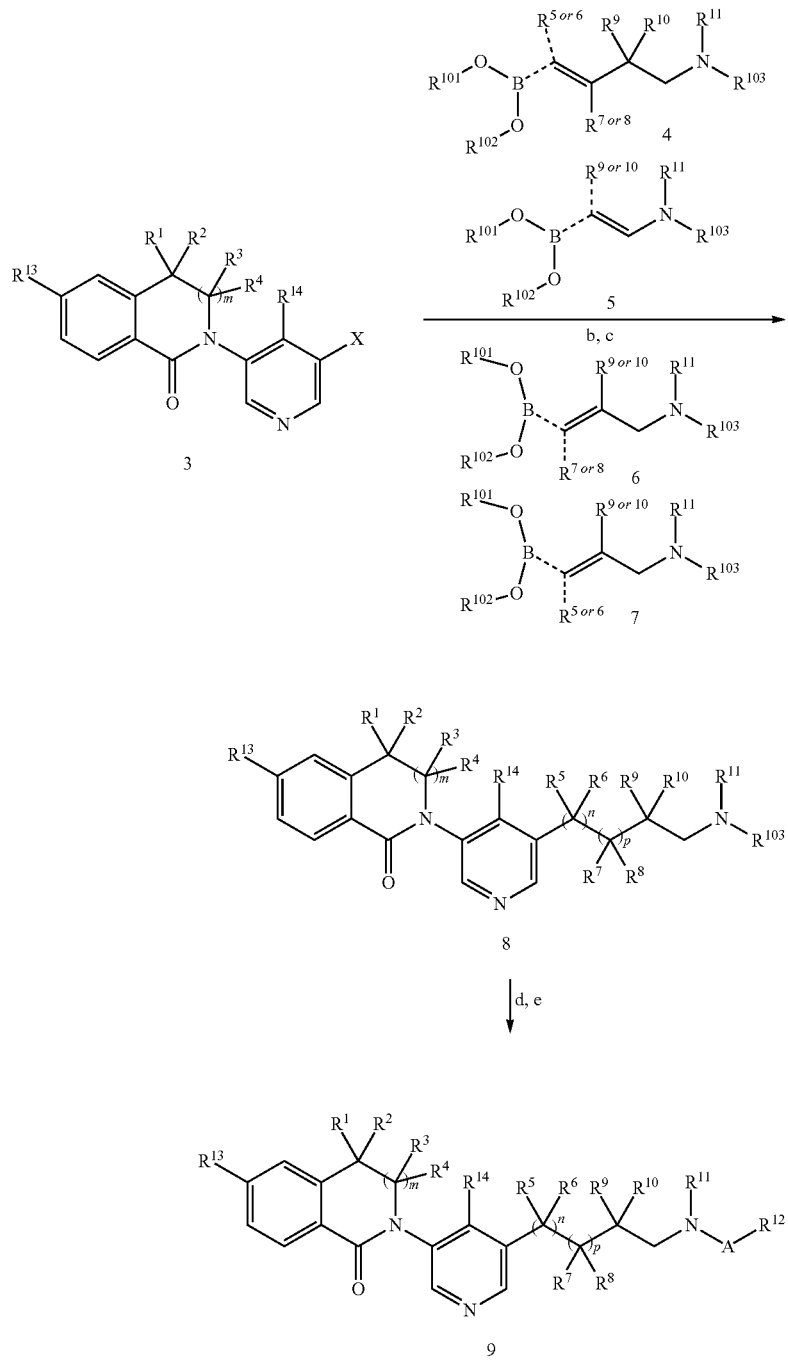
X is halogen or OSO$_2$CF$_3$
R$^{101}$ and R$^{102}$ are H or alkyl, or R$^{101}$ and R$^{102}$ together with the boron atom to which they are attached form 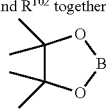
R$^{103}$ is a suitable protecting group or A—R$^{12}$ Scheme 1b

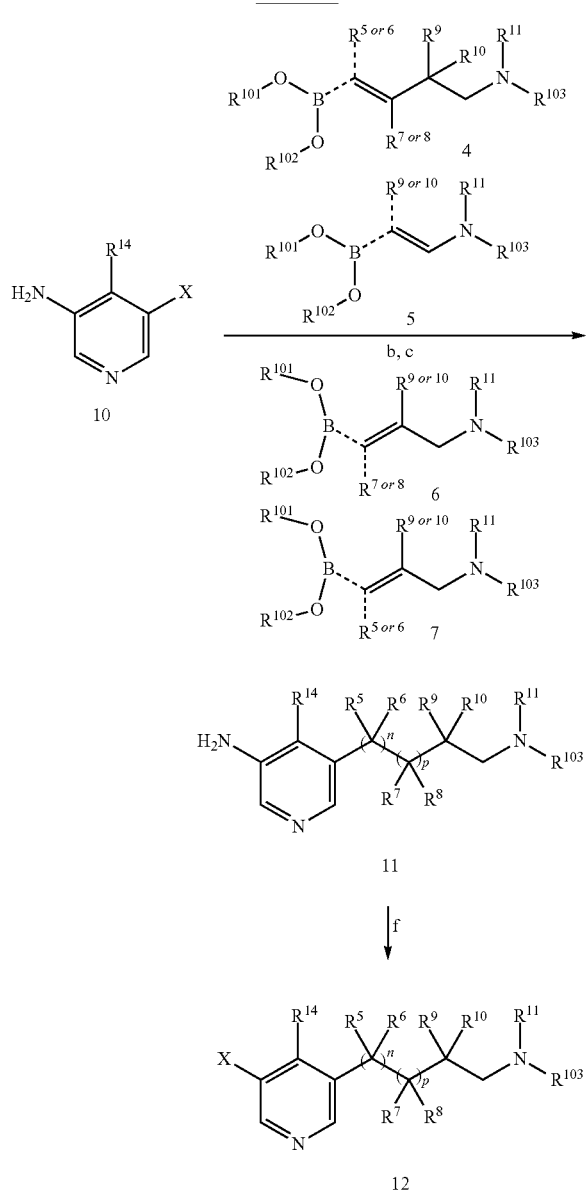

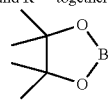

X is halogen or OSO₂CF₃
R¹⁰¹ and R¹⁰² are H or alkyl, or R¹⁰¹ and R¹⁰² together with the boron atom to which they are attached form R¹⁰³ is a suitable protecting group or A—R¹²

Scheme 1c

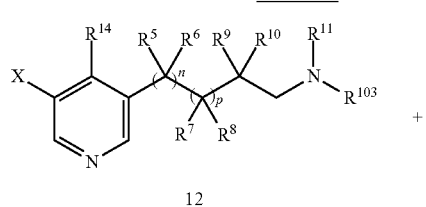

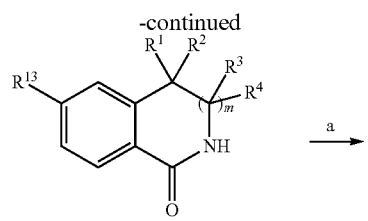

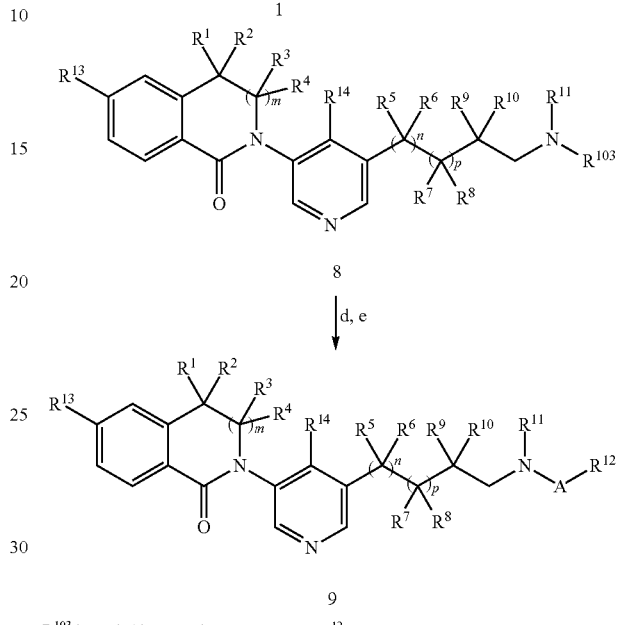

R¹⁰³ is a suitable protecting group or A—R¹²

Carbamates 101 (Scheme 2a) react with polyphosphoric acid at elevated temperature (e.g. 100-180° C.) to form 3,4-dihydro-2H-isoquinolin-1-one derivatives 102 (step a). Trifluoroacetamides 103 can be cyclized to 1-(3,4-dihydro-1H-isoquinolin-2-yl)-2,2,2-trifluoro-ethanone compounds 104 by treatment with paraformaldehyde in a mixture of concentrated sulfuric acid and acetic acid preferably around room temperature (step b). Removal of the trifluoroacteyl group by treatment with e.g. potassium hydroxide in a solvent like ethanol at temperatures around room temperature gives tetrahydro-isoquinoline compounds 105 (step c). Oxidation of tetrahydro-isoquinoline compounds 105 e.g. with iodoso benzene and potassium bromide preferably in water gives 3,4-dihydro-2H-isoquinolin-1-one compounds 102 (step d). Reaction of isoindole-1,3-dione compounds 106 (Scheme 2b) with a Grignard reagent R¹MgX in a solvent like THF preferably around 0° C. gives adducts 107 (step e). Subsequent treatment with triethylsilane and boron trifluoride etherate in a solvent like dichloromethane and in a temperature range preferably between −25° C. and RT gives isoindolone compounds 108 (step f). Introduction a methoxybenzyl protecting group into isoindolone compounds 109 (e.g. by treatment with sodium bis(trimethylsilyl)amide and 1-bromomethyl-4-methoxy-benzene in THF between 0° C. and RT) gives protected compounds 110 (step g); similarly, a methoxybenzyl protecting group can be introduced into compounds 108. Treatment of compounds 108 carrying an additional methoxybenzyl protecting group or compounds 110 with a base like sodium hydride in a solvent like THF and then with an alkyl halide, mesylate or tosylate preferably between RT and the reflux temperature of the solvent gives compounds 111 with structurally different or structurally identical $R^1$ and $R^2$ groups (step h). Alternatively, treatment of compounds 108 carrying an additional methoxybenzyl protecting group or compounds 110 with a base like NaH, LDA or LiHMDS in solvents like DMF, tetrahydrofuran or 1,2-dimethoxyethane and then with one or sequentially with two different alkyl halides, mesylates or tosylates preferably between −78° C. and the reflux temperature of the solvent gives compounds 111 with structurally different or structurally identical $R^1$ and $R^2$ groups (step h). Removal of the protecting group, e.g. by treatment with trifluoroacetic acid at elevated temperature gives isoindolone compounds 112 (step i). Alternatively (Scheme 2c), compounds 114 with $R^1$ and $R^2$ being alkyl groups can be obtained from cyano compounds 113 and suitable Grignard reagents, either by addition of two different reagents sequentially or a single Grignard reagent in excess (to obtain compounds with identical $R^1$ and $R^2$) preferably in the presence of titanium tetra-isopropoxide in solvents like THF preferably in a temperature range between 0° C. and RT (step k). Compounds 114 with $R^1$=H and $R^2$ being an alkyl group can be obtained from cyano compounds 113 and suitable Grignard reagents in solvents like THF preferably in a temperature range between 0° C. and RT (step k) followed by reduction of the imine formed with sodium borohydride in e.g. methanol around RT (step k). Compounds 114 undergo ring closure by reactions with catalysts like dichloro[1,1'-bis(diphenylphosphino)-ferrocene]palladium (II) in solvents like DMF in the presence of a base like $iPr_2NEt$ preferably in a temperature range between about 100° C. and 150° C. in autoclave in the presence of carbon monoxide to form compounds 115 (step l).

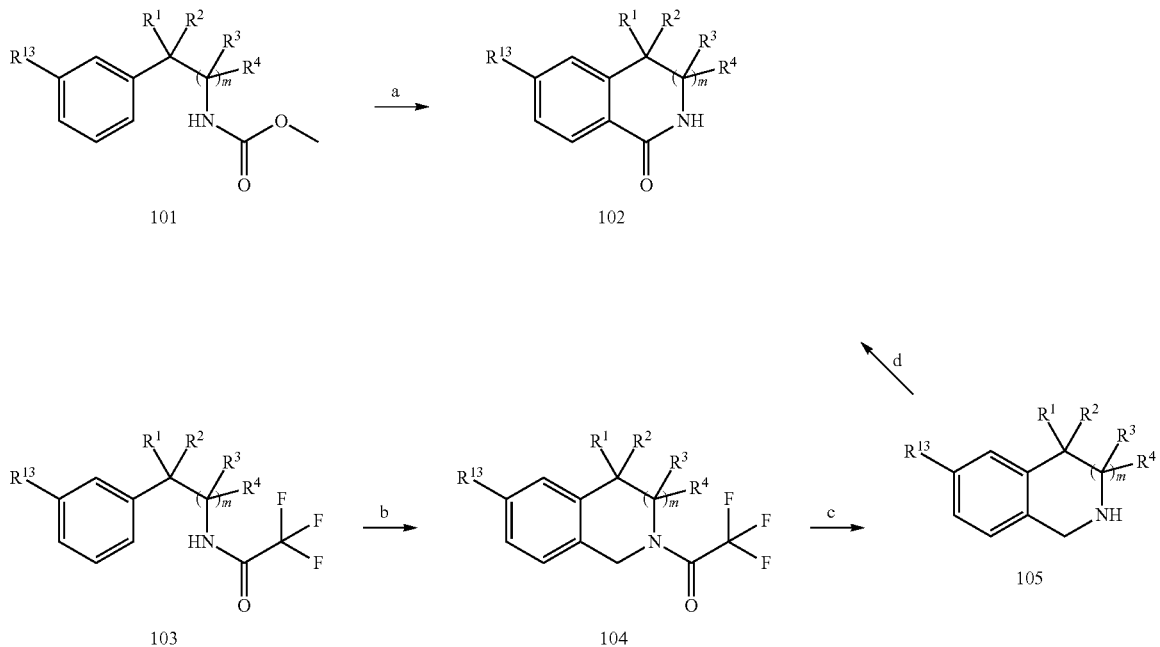

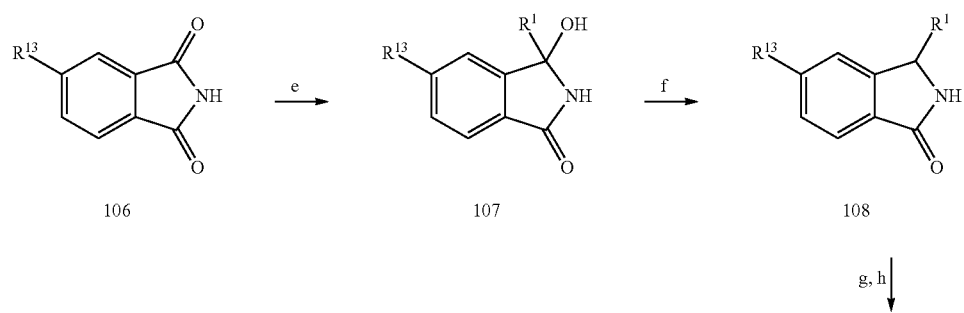

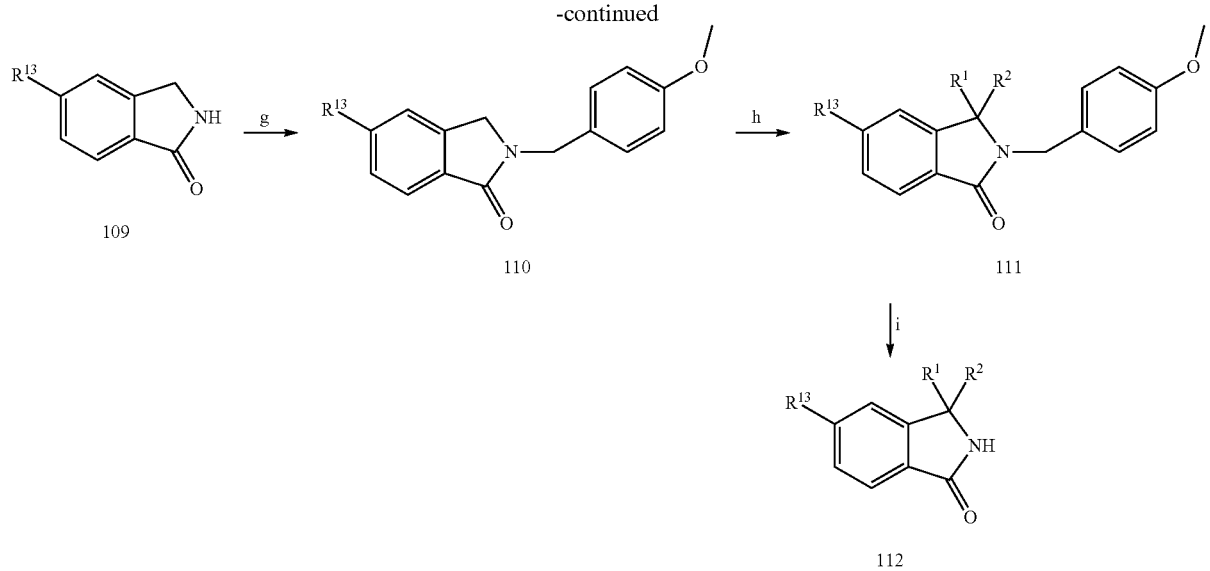

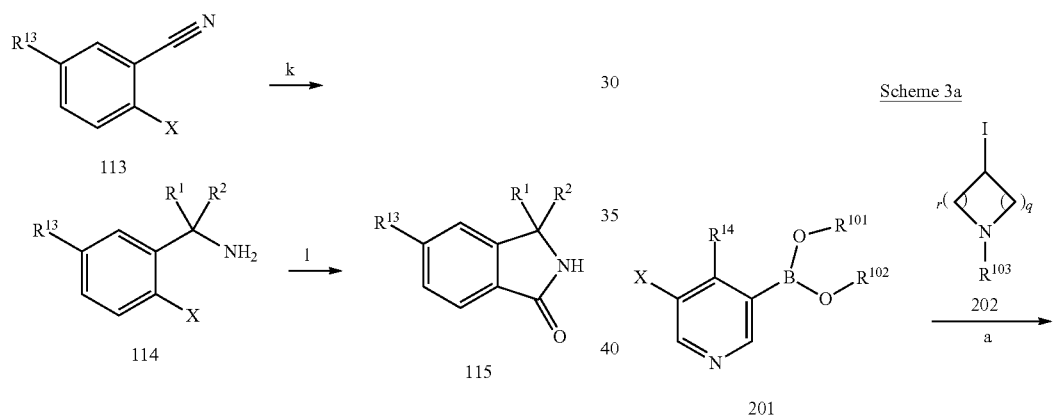

Additional and alternative options for preparation of compounds 12 (Scheme 1b) are depicted in Schemes 3a and 3b:

Pyridine boronic ester compounds 201 react with iodo compounds 202 in the presence of NiI$_2$ and trans-2-amino-cyclohexanol hydrochloride as catalysts and a base like sodium hexamethyl-disilazide in a solvent like isopropanol preferably around 80° C. preferably under microwave irradiation to give adducts 203 (step a).

Iodo compounds 202, when treated with zink dust, TMSCl, 1, 2 dibromoethane in a solvent like dimethylacetamide followed by reaction with a dihalopyridine compound 204 in the presence of CuI and PdCl$_2$(dppf) at temperatures around 100° C. gives adducts 203 (step b).

Dihalo-pyridine compounds 204 react with carbonyl compounds 205 in the presence of n-BuLi in solvents like THF or ether at temperatures between −78° C. and RT to give adducts 206 (step c). Treatment of adducts 206 with reagents like DAST or SOCl$_2$ then transforms the OH function into a halogen atom to give compounds 207 (step d).

Dihalo-pyridine compounds 204 react with olefins 208 in the presence of formic acid, a base like triethylamine and a catalyst like tetrakis(triphenylphosphine)palladium(0) in solvents like DMF at temperatures around 100° C. to give adducts 209 and 210 (step e).

Thus, compounds 203, 206, 207, 209 and 210 represent further examples of compounds 12 (Schemes 1).

Scheme 3a

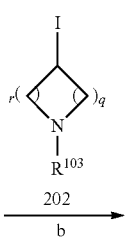

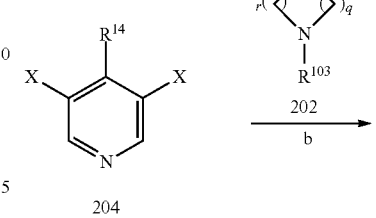

-continued

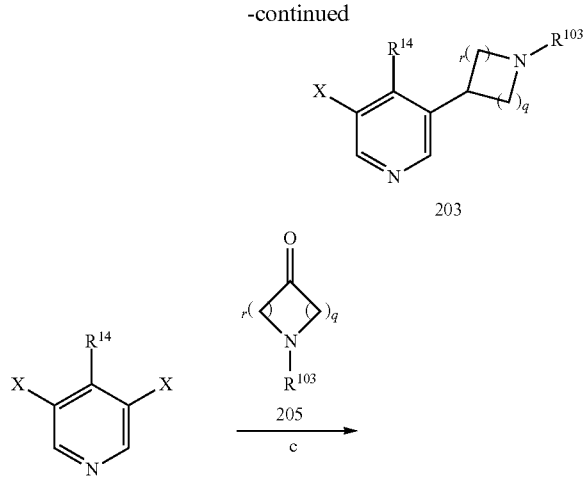

203

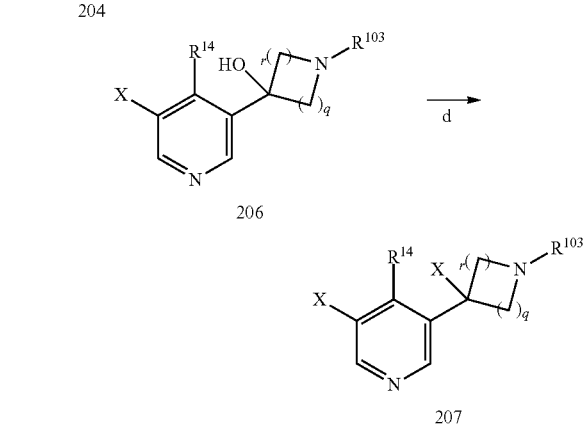

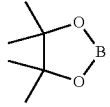

207

X is halogen or OSO$_2$CF$_3$
R$^{101}$ and R$^{102}$ are H or alkyl, or R$^{101}$ and R$^{102}$ together with the boronatom to which they are attached form R$^{103}$ is a suitable protecting group or A—R$^{12}$
r and q are independently selected from 1 and 2

Scheme 3b

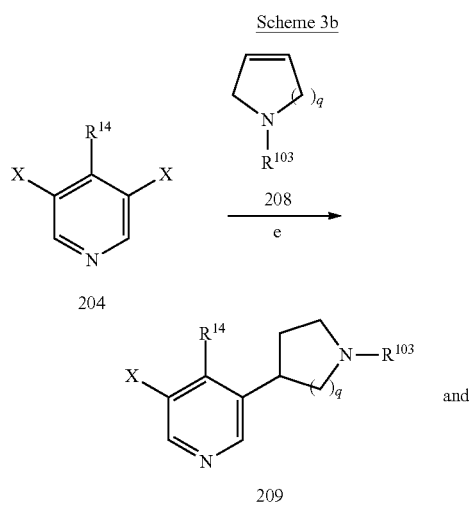

-continued

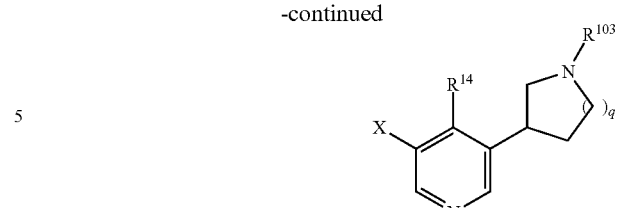

210

X is halogen or OSO$_2$CF$_3$
R$^{103}$ is a suitable protecting group or A—R$^{12}$
q is 1 or 2

Also an embodiment of the present invention is a process to prepare a compound of formula (I) as defined above comprising the reaction of a compound of formula (II) in the presence of a compound of formula (III);

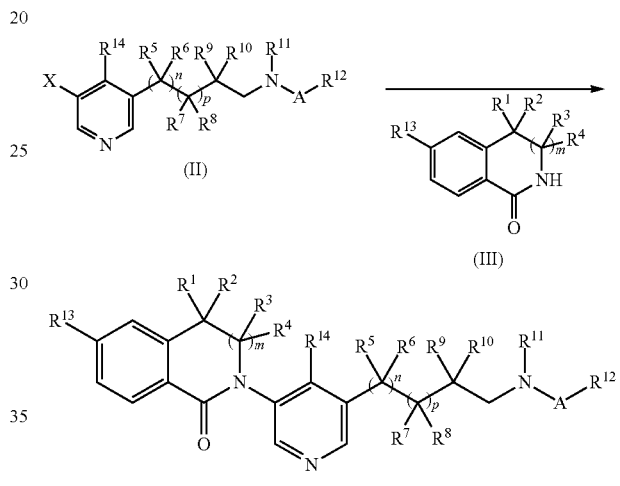

wherein R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, A, m, n and p are as described herein and X is halogen or triflate.

In particular, in the presence of copper (I) iodide, potassium or cesium carbonate, a chelating 1,2-diamino compound like N,N'-dimethylethylenediamine or trans-1,2-diamino-cyclohexane, at elevated temperatures, preferable with the aid of microwave heating and in solvents like 1,4-dioxane.

Also an object of the present invention is a compound according to formula (I) as described herein for use as therapeutically active substance.

Likewise an object of the present invention is a pharmaceutical composition comprising a compound according to formula (I) as described herein and a therapeutically inert carrier.

The present invention also relates to the use of a compound according to formula (I) as described herein for the treatment or prophylaxis of chronic kidney disease, congestive heart failure, hypertension, primary aldosteronism and Cushing syndrom.

The present invention also relates to the use of a compound according to formula (I) as described herein for the treatment or prophylaxis of diabetic nephropathy.

The present invention also relates to the use of a compound according to formula (I) as described herein for the treatment or prophylaxis of kidney or heart fibrosis.

The present invention also relates to the use of a compound according to formula (I) as described herein for the treatment or prophylaxis of chronic kidney disease.

The present invention also relates to the use of a compound according to formula (I) as described herein for the treatment or prophylaxis of congestive heart failure.

The present invention also relates to the use of a compound according to formula (I) as described herein for the treatment or prophylaxis of hypertension.

The present invention also relates to the use of a compound according to formula (I) as described herein for the treatment or prophylaxis of primary aldosteronism.

A particular embodiment of the present invention is a compound according to formula (I) as described herein for the treatment or prophylaxis of chronic kidney disease, congestive heart failure, hypertension, primary aldosteronism and Cushing syndrom.

Also a particular embodiment of the present invention is a compound according to formula (I) as described herein for the treatment or prophylaxis of diabetic nephropathy.

Another particular embodiment of the present invention is a compound according to formula (I) as described herein for the treatment or prophylaxis of kidney or heart fibrosis.

Also a particular embodiment of the present invention is a compound according to formula (I) as described herein for the treatment or prophylaxis of chronic kidney disease.

Also a particular embodiment of the present invention is a compound according to formula (I) as described herein for the treatment or prophylaxis of congestive heart failure.

Also a particular embodiment of the present invention is a compound according to formula (I) as described herein for the treatment or prophylaxis of hypertension.

Also a particular embodiment of the present invention is a compound according to formula (I) as described herein for the treatment or prophylaxis of primary aldosteronism.

The present invention also relates to the use of a compound according to formula (I) as described herein for the preparation of a medicament for the treatment or prophylaxis of chronic kidney disease, congestive heart failure, hypertension, primary aldosteronism and Cushing syndrom.

The present invention also relates to the use of a compound according to formula (I) as described herein for the preparation of a medicament for the treatment or prophylaxis of diabetic nephropathy.

The present invention also relates to the use of a compound according to formula (I) as described herein for the preparation of a medicament for the treatment or prophylaxis of kidney or heart fibrosis.

Also an embodiment of the present invention is the use of a compound according to formula (I) as described herein for the preparation of a medicament for the treatment or prophylaxis of chronic kidney disease.

Also an embodiment of the present invention is the use of a compound according to formula (I) as described herein for the preparation of a medicament for the treatment or prophylaxis of congestive heart failure.

Also an embodiment of the present invention is the use of a compound according to formula (I) as described herein for the preparation of a medicament for the treatment or prophylaxis of hypertension.

Also an embodiment of the present invention is the use of a compound according to formula (I) as described herein for the preparation of a medicament for the treatment or prophylaxis of primary aldosteronism.

Also an object of the invention is a method for the treatment or prophylaxis of chronic kidney disease, congestive heart failure, hypertension, primary aldosteronism and Cushing syndrom, which method comprises administering an effective amount of a compound according to formula (I) as described herein.

Also an object of the invention is a method for the treatment or prophylaxis of diabetic nephropathy, which method comprises administering an effective amount of a compound according to formula (I) as described herein.

Also an object of the invention is a method for the treatment or prophylaxis of kidney or heart fibrosis, which method comprises administering an effective amount of a compound according to formula (I) as described herein.

Also an embodiment of the present invention is a method for the treatment or prophylaxis of chronic kidney disease, which method comprises administering an effective amount of a compound according to formula (I) as described herein.

Also an embodiment of the present invention is a method for the treatment or prophylaxis of congestive heart failure, which method comprises administering an effective amount of a compound according to formula (I) as described herein.

Also an embodiment of the present invention is a method for the treatment or prophylaxis of hypertension, which method comprises administering an effective amount of a compound according to formula (I) as described herein.

Also an embodiment of the present invention is a method for the treatment or prophylaxis of primary aldosteronism, which method comprises administering an effective amount of a compound according to formula (I) as described herein.

Also an embodiment of the present invention is a compound of formula (I) as described herein, when manufactured according to any one of the described processes.

Assay Procedures

Herein we identified the use of the G-402 cell line as a host cell to ectopically express (transiently or stably) enzymes of the CYP11 family. Specifically we developed stable G-402 cells expressing ectopically human CYP11B1, human CYP11B2, human CYP11A1, cynmolgus CYP11B1 or cynomolgus CYP11B2 enzyme activity. Importantly the identified cell line G-402 expresses co-factors (adrenodoxin and adrenodoxin reductase) important for the activity of the CYP11 family and no relevant enzyme activity of the CYP11 family (in comparison to H295R cells) was detected in these cells. Therefore the G-402 cell line is uniquely suited as a host cell for the ectopic expression of enzymes from the CYP11 family. G-402 cells can be obtained from ATCC (CRL-1440) and were originally derived from a renal leiomyoblastoma.

The expression plasmids contains the ORF for either human/cyno CYP11B1 or CYP11B2 under the control of a suitable promoter (CMV-promoter) and a suitable resistance marker (neomycin). Using standard techniques the expression plasmid is transfected into G-402 cells and these cells are then selected for expressing the given resistance markers. Individual cell-clones are then selected and assessed for displaying the desired enzymatic activity using 11-Deoxycorticosterone (Cyp11B2) or 11-Deoxycortisol (Cyp11B) as a substrate.

G-402 cells expressing CYP11 constructs were established as described above and maintained in McCoy's 5a Medium Modified, ATCC Catalog No. 30-2007 containing 10% FCS and 400 µg/ml G418 (Geneticin) at 37° C. under an atmosphere of 5% CO2/95% air. Cellular enzyme assays were performed in DMEM/F12 medium containing 2.5% charcoal treated FCS and appropriate concentration of substrate (0.3-10 uM 11-Deoxycorticosterone, 11-Deoxycortisol or Corticosterone). For assaying enzymatic activity, cells were plated onto 96 well plates and incubated for 16 h. An aliquot of the supernatant is then transferred and analyzed for the concentration of the expected product (Aldosterone for CYP11B2; Cortisol for CYP11B1). The concentrations of these steroids can be determined using HTRF assays from CisBio analyzing either Aldosterone or Cortisol.

Inhibition of the release of produced steroids can be used as a measure of the respective enzyme inhibition by test compounds added during the cellular enzyme assay. The dose dependent inhibition of enzymatic activity by a compound is calculated by means of plotting added inhibitor concentrations (x-axes) vs. measured steroid/product level (y-axes). The inhibition is then calculated by fitting the following 4-parameter sigmoidal function (Morgan-Mercer-Flodin (MMF) model) to the raw data points using the least squares method:

$$y = \frac{AB + Cx^D}{B + x^D}$$

wherein, A is the maximum y value, B is the EC50 factor determined using XLFit, C is the minimum y value and D is the slope value.

The maximum value A corresponds to the amount of steroid produced in the absence of an inhibitor, the value C corresponds to the amount of steroid detected when the enzyme is fully inhibited.

EC50 values for compounds claimed herein were tested with the G402-based assay system described. Cyp11B2 enzyme activity was tested in presence of 1 μM Deoxycorticosterone and variable amounts of inhibitors; Cyp11B1 enzyme activity was tested in presence of 1 μM Deoxycortisol and variable amounts of inhibitors.

| Example | EC50 human CYP11B2 nM | EC50 human CYP11B1 nM |
|---|---|---|
| 1 | 5 | 238 |
| 2 | 2 | 290 |
| 3 | 2 | 53 |
| 4 | 6 | 605 |
| 5 | 5 | 213 |
| 6 | 15 | 332 |
| 7 | 2 | 149 |
| 8 | 4 | 109 |
| 9 | 14 | 800 |
| 10 | 2 | 93 |
| 11 | 7 | 601 |
| 12 | 2 | 75 |
| 13 | 19 | 957 |
| 14 | 4 | 232 |
| 15 | 1 | 239 |
| 16 | 4 | 1194 |
| 17 | 3 | 1003 |
| 18 | 16 | 219 |
| 19 | 21 | 1339 |
| 20 | 8 | 488 |
| 21 | 25 | 1052 |
| 22 | 84 | 7342 |
| 23 | 97 | 949 |
| 24 | 2 | 433 |
| 25 | 2 | 107 |
| 26 | 11 | 1622 |
| 27 | 1 | 523 |
| 28 | 4 | 167 |
| 29 | 9 | 117 |
| 30 | 1 | 153 |
| 31 | 1.5 | 772 |
| 32 | 7 | 616 |
| 33 | 148 | 4546 |
| 34 | 13 | 492 |
| 35 | 8 | 325 |
| 36 | 18 | 1404 |
| 37 | 2 | 98 |
| 38 | 1 | 575 |
| 39 | 9 | 1850 |
| 40 | 19 | 2423 |
| 41 | 35 | 986 |
| 42 | 34 | 8073 |
| 43 | 21 | 1903 |
| 44 | 4 | 8 |
| 45 | 30 | 1251 |
| 46 | 23 | 1925 |
| 47 | 41 | 573 |
| 48 | 35 | 1715 |
| 49 | 151 | 1320 |

Compounds of formula (I) and their pharmaceutically acceptable salts or esters thereof as described herein have $EC_{50}$ (CYP11B2) values between 0.000001 uM and 1000 uM, particular compounds have $EC_{50}$ (CYP11B2) values between 0.00005 uM and 500 uM, further particular compounds have $EC_{50}$ (CYP11B2) values between 0.0005 uM and 50 uM, more particular compounds have $EC_{50}$ (CYP11B2) values between 0.0005 uM and 5 uM. These results have been obtained by using the described enzymatic assay.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, drages, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, drages and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

In accordance with the invention, the compounds of formula (I) or their pharmaceutically acceptable salts and esters can be used for the treatment or prophylaxis of aldosterone mediated diseases.

The compounds of formula (I) or their pharmaceutically acceptable salts and esters herein are inhibitors of CYP11B2. The compounds of formula (I) or their pharmaceutically acceptable salts and esters herein display also variable inhibition of CYP11B1 but present an improved selectivity towards CYP11B2 versus CYP11B1. Such compounds may be used for treatment or prophylaxis of conditions displaying excessive cortisol production/levels or both excessive cortisol and aldosterone levels (for ex. Cushing syndrome, burn trauma patients, depression, post-traumatic stress disorders, chronic stress, corticotrophic adenomas, Morbus Cushing).

In accordance with the invention, the compounds of formula (I) or their pharmaceutically acceptable salts and esters can be used for the treatment or prophylaxis of cardiovascular conditions (including hypertension and heart failure), vascular conditions, endothelial dysfunction, baroreceptor dysfunction, renal conditions, liver conditions, fibrotic diseases, inflammatory conditions, retinopathy, neuropathy (such as peripheral neuropathy), pain, insulinopathy, edema, edematous conditions, depression and the like.

Cardiovascular conditions include congestive heart failure, coronary heart disease, arrhythmia, arterial fibrillation, cardiac lesions, decreased ejection fraction, diastolic and systolic heart dysfunction, fibrinoid necrosis of coronary arteries, cardiac fibrosis, hypertrophic cardiomyopathy, impaired arterial compliance, impaired diastolic filling, ischemia, left ventricular hypertrophy, myocardial and vascular fibrosis, myocardial infarction, myocardial necrotic lesions, cardiac arrhythmias, prevention of sudden cardiac death, restenosis, stroke, vascular damage.

Renal conditions include acute and chronic renal failure, nephropathy, end-stage renal disease, diabetic nephropathy, decreased creatinine clearance, decreased glomerular filtration rate, expansion of reticulated mesangial matrix with or without significant hypercellularity, focal thrombosis of glomerular capillaries, global fibrinoid necrosis, glomerulosclerosis, ischemic lesions, malignant nephrosclerosis (such as ischemic retraction, microalbuminuria, proteinuria, reduced renal blood flow, renal arteriopathy, swelling and proliferation of intracapillary (endothelial and mesangial) and/or extracapillary cells (crescents).

Renal conditions also include glomerulonephritis (such as diffuse proliferative, focal proliferative, mesangial proliferative, membranoproliferative, minimal change membranous glomerulonephritis), lupus nephritis, non-immune basement membrane abnormalities (such as Alport syndrome), renal fibrosis and glomerulosclerosis (such as nodular or global and focal segmental glomerulosclerosis).

Liver conditions include, but are not limited to, liver steatosis, nonalcoholic steatohepatitis, liver cirrhosis, liver ascites, hepatic congestionand the like.

Vascular conditions include, but are not limited to, thrombotic vascular disease (such as mural fibrinoid necrosis, extravasation and fragmentation of red blood cells, and luminal and/or mural thrombosis), proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction, and the like.

Inflammatory conditions include, but are not limited to, arthritis (for example, osteoarthritis), inflammatory airways diseases (for example, chronic obstructive pulmonary disease (COPD)), and the like.

Pain includes, but is not limited to, acute pain, chronic pain (for example, arthralgia), and the like.

Edema includes, but is not limited to, peripheral tissue edema, hepatic congestion, liver ascites, splenic congestion, respiratory or lung congestion, and the like.

Insulinopathies include, but are not limited to, insulin resistance, Type I diabetes mellitus, Type II diabetes mellitus, glucose sensitivity, pre-diabetic state, pre-diabetes, syndrome X, and the like.

Fibrotic diseases include, but are not limited to myocardial and intrarenal fibrosis, renal interstitial fibrosis and liver fibrosis.

Furthermore, the compounds of formula (I) or their pharmaceutically acceptable salts and esters as described herein can also be used for the treatment or prophylaxis of cardiovascular condition selected from the group consisting of hypertension, heart failure (particularly heart failure post myocardial infarction), left ventricular hypertrophy, and stroke.

In another embodiment, the cardiovascular condition is hypertension.

In particular embodiment, the cardiovascular condition is treatment-resistant hypertension.

In another embodiment, the cardiovascular condition is heart failure.

In another embodiment, the cardiovascular condition is left ventricular hypertrophy.

In another embodiment, the cardiovascular condition is congestive heart failure, more particularly in patients with preserved left ventricular ejection fraction.

In another embodiment, the cardiovascular condition is stroke.

In another embodiment, the compounds of formula (I) or their pharmaceutically acceptable salts and esters can be used for the treatment or prophylaxis renal condition.

In another embodiment, the renal condition is nephropathy.

In another embodiment, the renal condition is auto-immune glomerulonephritis.

In another embodiment, the chronic kidney disease is diabetic nephropathy.

In another embodiment, the fibrotic disease is kidney or heart fibrosis.

In another embodiment, the compounds of formula (I) or their pharmaceutically acceptable salts and esters can be used for the treatment or prophylaxis Type II diabetes mellitus.

In another embodiment, the compounds of formula (I) or their pharmaceutically acceptable salts and esters can be used for the treatment or prophylaxis Type I diabetes mellitus.

In another embodiment, the compounds of formula (I) or their pharmaceutically acceptable salts and esters can be used for the treatment or prophylaxis of diabetic retinopathy.

The invention is illustrated hereinafter by Examples, which have no limiting character.

In case the preparative examples are obtained as a mixture of enantiomers, the pure enantiomers can be separated by methods described herein or by methods known to the man skilled in the art, such as e.g. chiral chromatography or crystallization.

EXAMPLES

All examples and intermediates were prepared under argon atmosphere if not specified otherwise.

Intermediate A-1

6-Chloro-3,4-dihydro-2H-isoquinolin-1-one

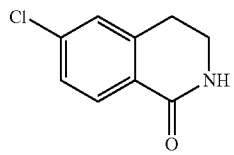 [SMILES: O=C1NCCc2cc(Cl)ccc21]

[A] [2-(3-Chloro-phenyl)-ethyl]-carbamic acid methyl ester

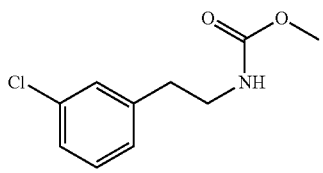

At 0° C., methyl chloroformate (4.6 g, 48 mmol) was added drop wise to a solution of 2-(3-chloro-phenyl)-ethylamine (5.0 g, 32 mmol) and Et$_3$N (6.4 g, 64 mmol) in DCM (100 mL). After the addition, the mixture was stirred at room temperature for 0.5 hours. The organic layer was washed with water (3×30 mL), 1N HCl (20 mL) and brine (30 mL), dried over anhy. Na$_2$SO$_4$, filtered and concentrated in vacuo. After vacuum drying, the title compound was obtained (6.49 g, 95%) as a white solid. MS: 214.1 (M+H)$^+$.

[B] 6-Chloro-3,4-dihydro-2H-isoquinolin-1-one

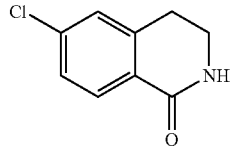 [SMILES: O=C1NCCc2cc(Cl)ccc21]

Under N$_2$ protection, a mixture of [2-(3-chloro-phenyl)-ethyl]-carbamic acid methyl ester (5.0 g, 23.4 mmol) and PPA (polyphosphoric acid) (20 g) in a 250 mL round-bottom flask was vigorously stirred at 120° C. for 2 hours. After cooling to room temperature, the reaction mixture was treated with ice-water and aqueous ammonia solution to adjust the pH to 8. Then, the mixture was extracted with EtOAc, and the organic layer was washed with brine, dried over anhy. Na$_2$SO$_4$ and filtered. After removal of solvent under reduced pressure, the crude product obtained was further washed with ethyl ether to give title compound (1.66 g, 39%) as a white solid. MS: 182.0 (M+H)$^+$.

Intermediate A-2

5-Chloro-3-methyl-2,3-dihydro-isoindol-1-one

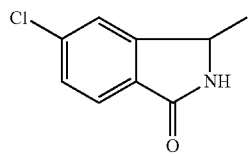

[A] 1-(2-Bromo-5-chloro-phenyl)-ethylamine

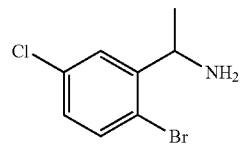

To a stirred solution of 2-bromo-5-chlorobenzonitrile (80 g, 370 mmol) in THF (1000 mL) at 0° C. was added EtMgBr (370 mL, 1110 mmol) drop wise. The reaction mixture was stirred at 0-5° C. for 5 hours before MeOH (500 mL) was added drop wise. After the solution was stirred for another 15 min, NaBH$_4$ (28 g, 740 mmol) was added carefully and the resulting mixture was stirred at room temperature for 16 hours. The reaction solution was then poured into water, exacted with EtOAc (3×). The organic combined layers were dried over anhy. Na$_2$SO$_4$, filtered and concentrated in vacuo to give a crude product, which was purified by column (petroleum ether: EtOAc=3:1) to afford title compound (30 g, 35%) as yellowish oil. MS: 235.5 (M+H)$^+$.

[B] 5-Chloro-3-methyl-2,3-dihydro-isoindol-1-one

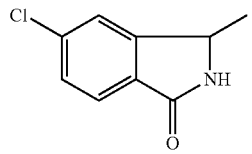

A mixture of 1-(2-bromo-5-chlorophenyl)ethanamine (30 g, 127.9 mmol), Pd(dppf)Cl$_2$ (3.2 g, 12.79 mmol), and DIPEA (49.5 g, 383.7 mmol) in DMF (1.2 L) was stirred in an autoclave under 2 MPa of CO at 130° C. for 24 hours. After it was cooled to room temperature, the reaction mixture was diluted with EtOAc (500 mL). The organic layer was washed with brine, filtered, and concentrated in vacuo to give a crude product which was purified by chromatography (petroleum ether: EtOAc=3:1) to give the title compound (5.2 g, 23%) as a brown solid. MS: 181.6 (M+H)⁺.

Intermediate A-3

5-Chloro-3,3-dimethyl-2,3-dihydro-isoindol-1-one

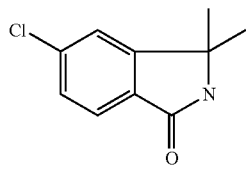

[A] 1-(2-Bromo-5-chloro-phenyl)-1-methyl-ethylamine

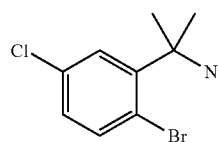

To a stirred solution of 2-bromo-5-chloro-benzonitrile (10 g, 46 mmol) in THF (200 mL) at 0° C., was added MeMgBr (77 mL, 230 mmol) drop wise. The reaction mixture was allowed to warm up to room temperature and stirred for 2 hours. Ti(Oi-Pr)₄ (13 g, 46 mmol) was added and the solution was stirred for another 16 hours before it was quenched with aq. HCl solution and washed with EtOAc. The aqueous phase was adjusted to pH~10 with aq. NaOH solution, and exacted with EtOAc (3×). The combined organic layers were concentrated to give a crude title product (3.8 g, 33%) as oil, which was used directly in the next step without further purification. MS: 249.30 (M+H)⁺.

[B] 5-Chloro-3,3-dimethyl-2,3-dihydro-isoindol-1-one

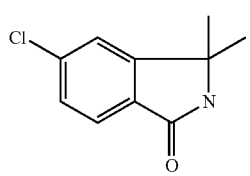

A mixture of 1-(2-bromo-5-chloro-phenyl)-1-methyl-ethylamine (3.8 g, 15.3 mmol), Pd(dppf)Cl₂ (0.4 g, 0.55 mmol) and DIPEA (6 g, 45.9 mmol) in DMF (20 mL) was stirred in an autoclave under 2 MPa of CO at 130° C. for 16 hours. After it was cooled to room temperature, the reaction mixture was diluted with EtOAc (300 mL). The organic layer was washed with brine (80 mL×2), filtered, and concentrated in vacuo to give a crude product which was purified by chromatography to give the title compound (1.13 g, 38%) as a brown solid. MS: 195.70 (M+H⁺)

Intermediate A-4

3,3-Dimethyl-1-oxo-2,3-dihydro-1H-isoindole-5-carbonitrile

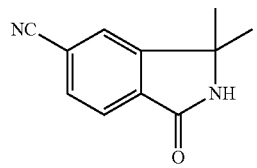

[A] 4-Bromo-2-methyl-benzoic acid methyl ester

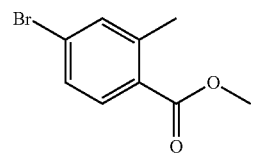

To a solution of 4-bromo-2-methyl-benzoic acid (30.0 g, 0.14 mol) in 115 mL of methanol was added thionyl chloride (20.25 mL, 0.28 mol) slowly and the reaction mixture was stirred at 70° C. for 2 hours before it was concentrated to afford a crude product which was then purified by column chromatography to give the title compound (30.03 g, 93.6%) as a solid.

[B] 4-Cyano-2-methyl-benzoic acid methyl ester

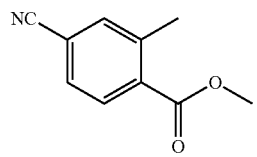

A mixture of 4-bromo-2-methyl-benzoic acid methyl ester (26.0 g, 113.5 mmol) and CuCN (12.48 g, 140.7 mmol) was heated at 180° C. for 5 hours before it was poured into ice-water. The solid precipitate was collected by vacuum filtration to give a crude product which was then purified by column chromatography to afford the title compound (12.53 g, 63%) as a solid.

[C] 2-Bromomethyl-4-cyano-benzoic acid methyl ester

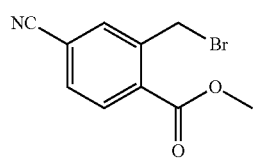

A mixture of 4-cyano-2-methyl-benzoic acid methyl ester (12.5 g, 71.35 mmol), NBS (12.7 g, 71.35 mmol) and di-benzoyl peroxide (BPO) (0.8 g, 3.28 mmol) in CCl₄ (200 mL) was heated to reflux temperature for 3 hours. Then, it was cooled to room temperature and the reaction mixture was filtered. The filtrate was concentrated in vacuo to give a crude product (18.2 g) which was used in the next step reaction without further purification.

[D] 2-(4-Methoxy-benzyl)-1-oxo-2,3-dihydro-1H-isoindole-5-carbonitrile

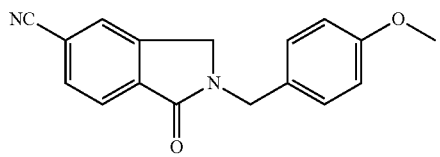 [SMILES: COc1ccc(CN2Cc3cc(C#N)ccc3C2=O)cc1]

To a solution of 2-bromomethyl-4-cyano-benzoic acid methyl ester (18.1 g, 71.24 mmol) in THF (300 mL) was added PMBNH₂ (23.4 g, 178.1 mmol) at 0° C. and the reaction mixture was stirred at room temperature for 16 hours. After vacuum filtration, the filtrate was concentrated in vacuo. The residue obtained was re-dissolved in EtOAc and washed with water and brine. The organic layer was dried over anhy. Na₂SO₄, filtered, and concentrated in vacuo to give a crude product which was purified by column chromatography to give the title compound (11.69 g, 56.0%) as a solid.

[E] 2-(4-Methoxy-benzyl)-3,3-dimethyl-1-oxo-2,3-dihydro-1H-isoindole-5-carbonitrile

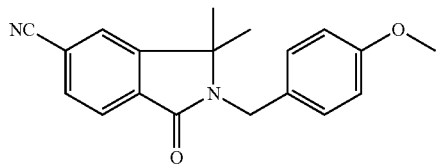 [SMILES: COc1ccc(CN2C(=O)c3ccc(C#N)cc3C2(C)C)cc1]

To a solution of 2-(4-methoxy-benzyl)-1-oxo-2,3-dihydro-1H-isoindole-5-carbonitrile (11.6 g, 41.7 mmol) in THF (300 mL) was added NaH (8.34 g, 208.4 mmol, 60% in mineral oil) and the reaction mixture was stirred at room temperature for 1 hour before iodomethane (35.5 g, 250.1 mmol) was added. After the addition, the reaction mixture was stirred at 70° C. for 2 hours until all the starting material was consumed. Then, it was cooled to room temperature, satd. aq. NH₄Cl solution was added and the mixture was extracted with EtOAc (200 mL×3). The combined organic layers were dried over anhy. MgSO₄, filtered, and concentrated under reduced pressure to give a crude product which was purified by column chromatography to afford the title compound (7.22 g, 56.5%) as a solid.

[F] 3,3-Dimethyl-1-oxo-2,3-dihydro-1H-isoindole-5-carbonitrile

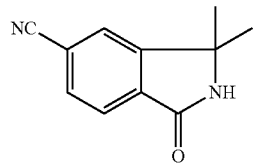

To a solution of 2-(4-methoxy-benzyl)-3,3-dimethyl-1-oxo-2,3-dihydro-1H-isoindole-5-carbonitrile (3.5 g, 11.42 mmol) in MeCN (70 mL) was added CAN (18.79 g, 34.27 mmol) in 30 mL of water at 0° C. The resulting reaction mixture was stirred at 0° C. for 1 hour until all the starting material was consumed. The reaction mixture was extracted between water and EtOAc and the combined organic layers were dried over anhy. MgSO₄, filtered, and concentrated under reduced pressure to give a crude product which was purified by column chromatography to afford the title compound (1.06 g, 49.8%) as a solid.

Intermediate A-5

2-Methoxy-7,7-dimethyl-6,7-dihydro-pyrrolo[3,4-b]pyridin-5-one

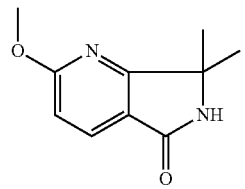

[A] 3-(Methoxycarbonyl)-2-methylpyridine 1-oxide

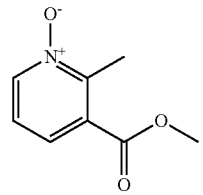

To a stirred solution of methyl-2-methylnicotinate (95 g, 629 mmol) in DCM (1.5 L) was added m-CPBA (119 g, 692 mmol) at 0° C. Then, the reaction mixture was stirred at room temperature for 16 hours; subsequently, it was washed with a mixture of satd. aq. Na₂SO₃ and NaHCO₃ solution. The organic layer was then dried over anhy. Na₂SO₄, filtered, and concentrated in vacuo to give a crude product (60 g, yield 57%), which was used in the next step reaction without further purification.

[B] Methyl 2-(chloromethyl)nicotinate

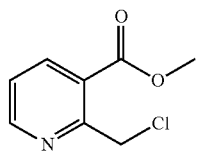

The crude 3-(methoxycarbonyl)-2-methylpyridine-1-oxide (35 g, 210 mmol) was added in small portion to POCl₃ (300 g) at room temperature. After the addition, the reaction mixture was refluxed for 3 hours before it was concentrated in vacuo. The residue was poured into ice-water, neutralized with aq. NaHCO₃ solution and extracted with AcOEt (125 mL×3). The combined organic layers were washed with brine, dried over anhy. Na₂SO₄, filtered, and concentrated in vacuo to afford a crude product which was then purified by column chromatography to give title compound (12 g, yield 30%).

[C] 2-(Chloromethyl)-3-(methoxycarbonyl)pyridine 1-oxide

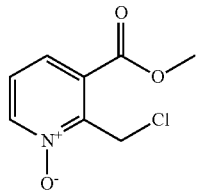

To a stirred solution of methyl-2-(chloromethyl)nicotinate (20 g, 108 mmol) in DCM (300 mL) was added m-CPBA (20.5 g, 119 mmol) at 0° C. Then, it was stirred at room temperature for 16 hours; subsequently, the reaction mixture was washed with a mixture of satd. aq. Na₂SO₃ and NaHCO₃ solution. The organic layer was dried over anhy. Na₂SO₄, filtered, and concentrated in vacuo to give the crude title product (20 g, yield 92%), which was used in the next step reaction without further purification.

[D] Methyl 6-chloro-2-(chloromethyl)nicotinate

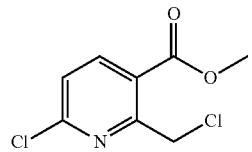

The crude of 2-(chloromethyl)-3-(methoxycarbonyl)pyridine-1-oxide (20 g, 99.5 mmol) was added in small portion to POCl₃ (200 g) at room temperature. The mixture was refluxed for 3 hours before it was concentrated in vacuo. The residue was poured into ice-water, neutralized with NaHCO₃ solution, and extracted with AcOEt (125 mL×3). The combined organic layers were concentrated to give the crude title product (17 g, yield 78%), which was used in the next step reaction without further purification.

[E] 2-Chloro-6-(4-methoxybenzyl)-6,7-dihydro-5H-pyrrolo[3,4-b]pyridin-5-one

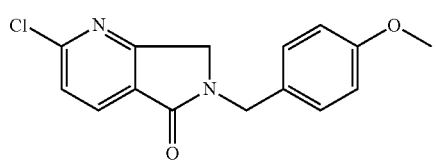 [SMILES: COc1ccc(CN2Cc3nc(Cl)ccc3C2=O)cc1]

To a stirred solution of crude methyl 6-chloro-2-(chloromethyl)nicotinate (10 g, 45.4 mmol) in THF (150 mL) was added PMBNH₂ (15.5 g, 113.5 mmol) at 0° C. The resulting reaction mixture was stirred at room temperature for 16 hours before it was concentrated under reduced pressure to give a crude product. After washing with MTBE (100 mL×3), the tilte compound was obtained (8.8 g, yield 67%) as a white solid. MS: 288.8 (M+H⁺, 1Cl).

[F] 2-Chloro-6-(4-methoxy-benzyl)-7,7-dimethyl-6,7-dihydro-pyrrolo[3,4-b]pyridin-5-one

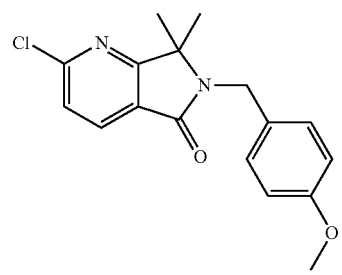 [SMILES: COc1ccc(CN2C(=O)c3ccc(Cl)nc3C2(C)C)cc1]

To a solution of 2-chloro-6-(4-methoxy-benzyl)-6,7-dihydro-pyrrolo[3,4-b]pyridin-5-one (5.8 g, 20.0 mmol) in THF (50 mL) was added sodium hydride (60% in mineral oil, 1.7 g, 42.0 mmol) at room temperature. The resulting reaction mixture was stirred for 30 min before iodomethane (6.0 g, 42.0 mmol) was added. After stirring at room temperature over night, the mixture was quenched with water and extracted with EtOAc. The organic layer was then washed with brine, dried over anhy. Na₂SO₄, filtered and concentrated in vacuo to give the crude product which was then purified by flash column chromatography (silica gel 20 g, 5% to 20% ethyl acetate in DCM). The title compound was obtained (3.8 g, 57%) as a white solid. MS: 316.2 (M+H⁺).

[G] 2-Methoxy-6-(4-methoxy-benzyl)-7,7-dimethyl-6,7-dihydro-pyrrolo[3,4-b]pyridin-5-one

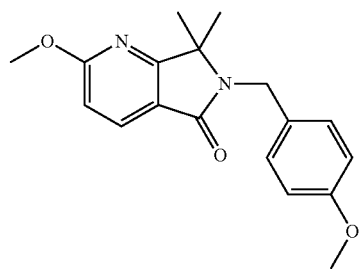 [SMILES: COc1ccc(CN2C(=O)c3ccc(OC)nc3C2(C)C)cc1]

To solution of 2-chloro-6-(4-methoxy-benzyl)-7,7-dimethyl-6,7-dihydro-pyrrolo[3,4-b]pyridin-5-one (3.15 g, 10 mmol) in DMF (30 mL) was added sodium methanolate (0.813 g, 15 mmol) at room temperature. The reaction mixture was stirred at room temperature for 4 hours, then quenched with water and extracted with EtOAc. The organic layer was washed with brine, dried over anhy. Na$_2$SO$_4$, filtered and concentrated in vacuo to give title compound (2.8 g, 90%) as a solid. MS: 313.1 (M+H$^+$).

[H] 2-Methoxy-7,7-dimethyl-6,7-dihydro-pyrrolo[3,4-b]pyridin-5-one

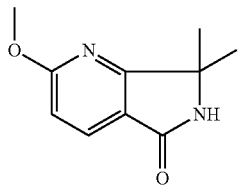

To solution of 2-methoxy-6-(4-methoxy-benzyl)-7,7-dimethyl-6,7-dihydro-pyrrolo[3,4-b]pyridin-5-one (0.31 g, 1.0 mmol) in CH$_3$CN (5 mL) was added ceric ammonium nitrate (1.64 g, 3.0 mmol) at room temperature. The reaction mixture was stirred at room temperature for 3 hours before water and EtOAc were added into the mixture. The organic layer was separated, dried over anhy. Na$_2$SO$_4$, filtered and concentrated in vacuo to give a crude product which was then purified by silica gel column chromatography to give the title compound (0.12 g, 63%) as a solid. MS: 193.1 (M+H$^+$).

Example 1

5-Chloro-3,3-dimethyl-2-[5-(1-propanoylpiperidin-4-yl)pyridin-3-yl]isoindol-1-one

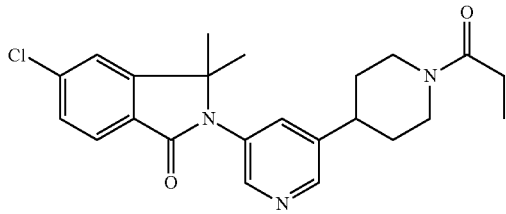 [SMILES: CCC(=O)N1CCC(c2cncc(N3C(=O)c4ccc(Cl)cc4C3(C)C)c2)CC1]

[A] 1-(3,6-Dihydro-2H-pyridin-1-yl)-propan-1-one

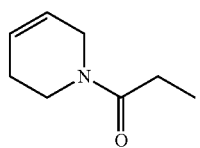

To a solution of 1,2,3,6-tetrahydro-piperidine (800 mg, 9.6 mmol) and triethylamine (1.82 g, 18 mmol) in DCM (20 mL) was added propionyl chloride (1.06 g, 11.5 mmol) drop wise. After the addition, the mixture was stirred for 30 minutes at room temperature before water was added. The organic layer was washed with satd. aq. sodium bicarbonate solution and brine in sequence and dried over anhy. Na$_2$SO$_4$. After removal of solvents, the crude product was obtained as yellow oil (1.1 g) and was used in the next step without further purification. MS: 140.1 (M+H)$^+$.

[B] 1-(5-Bromo-3',4',5',6'-tetrahydro-2'H-[3,4']bipyridinyl-1'-yl)-propan-1-one

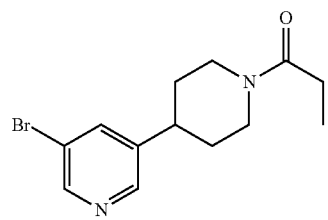 [SMILES: CCC(=O)N1CCC(c2cncc(Br)c2)CC1]

A mixture of 1-(3,6-dihydro-2H-pyridin-1-yl)-propan-1-one (708 mg, 5.1 mmol), 3-bromo-5-iodo-pyridine (2.5 g, 8.8 mmol), triethyl amine (1.03 g, 10.2 mmol), formic acid (350 mg, 7.65 mmol) and tetrakis(triphenylphosphine)palladium(0) (360 mg, 0.51 mmol) in DMF (12 mL) was stirred for overnight at 90° C. under nitrogen. After cooling to room temperature, the mixture was treated with water and extracted with ethyl acetate. The organic layer was dried over anhy. Na$_2$SO$_4$. After removal of solvents, the residue was purified by flash chromatography to afford the title compound as a mixture with its minor regioisomer (ratio=ca. 9:1) and as a yellow oil (200 mg). MS: 298.6 (M+H)$^+$.

[C] 5-Chloro-3,3-dimethyl-2-[5-(1-propanoylpiperidin-4-yl)pyridin-3-yl]isoindol-1-one

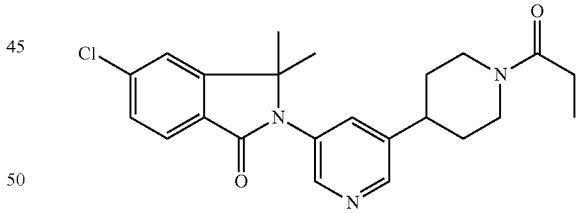

A mixture of 5-chloro-3,3-dimethyl-2,3-dihydro-isoindol-1-one (intermediate A-3, 200 mg, 1.02 mmol), 1-(5-bromo-3',4',5',6'-tetrahydro-2'H-[3,4']bipyridinyl-1'-yl)-propan-1-one (200 mg, 0.67 mmol), CuI (40 mg, 0.21 mmol), (1S,2S)-cyclohexane-1,2-diamine (48 mg, 0.42 mmol) and Cs$_2$CO$_3$ (460 mg, 1.41 mmol) were dissolved in dioxane (5 mL). The reaction mixture was subjected to microwave reaction at 150° C. for 2.5 hours before it was poured into aq. NaHCO$_3$ (20 mL) and extracted with EtOAc (30 mL, 3×). The combined organic layers were washed with brine, dried over anhy. Na$_2$SO$_4$, filtered and concentrated in vacuo to give a crude product which was then purified by Prep-HPLC to yield the title compound (36 mg, 13%) as a white solid. MS: 412.3 (M+H)$^+$.

Example 2

5-Chloro-2-[5-(1-ethylsulfonylpiperidin-4-yl)pyridin-3-yl]-3,3-dimethylisoindol-1-one

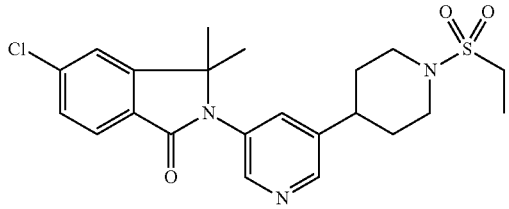

[A] 1-Ethanesulfonyl-1,2,3,6-tetrahydro-pyridine

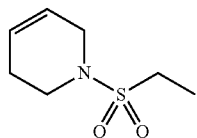

In analogy to the procedure described for the preparation of example 1[A], ethanesulfonyl chloride was used to yield a crude product as a white solid (89%). MS: 176.1 (M+H)$^+$.

[B] 5-Bromo-1'-ethanesulfonyl-1',2',3',4',5',6'-hexahydro-[3,4']bipyridinyl

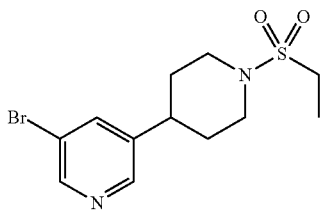 [SMILES: CCS(=O)(=O)N1CCC(c2cncc(Br)c2)CC1]

In analogy to the procedure described for the preparation of example 1[B], 1-ethanesulfonyl-1,2,3,6-tetrahydro-pyridine was used to yield the tile compound as a mixture with its regioisomer (ratio: ca 1:1) and as yellowish oil (250 mg). MS: 335.1 (M+H)$^+$.

[C] 5-Chloro-2-[5-(1-ethylsulfonylpiperidin-4-yl)pyridin-3-yl]-3,3-dimethylisoindol-1-one

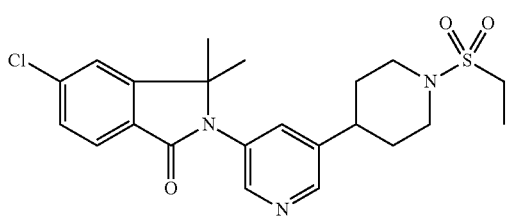 [SMILES: CCS(=O)(=O)N1CCC(c2cncc(N3C(=O)c4ccc(Cl)cc4C3(C)C)c2)CC1]

In analogy to the procedure described for the preparation of example 1[C], 5-bromo-1'-ethanesulfonyl-1',2',3',4',5',6'-hexahydro-[3,4']bipyridinyl was used to yield the title compound (9 mg) as a white solid. MS: 448.2 (M+H)$^+$.

Example 3

5-Chloro-3,3-dimethyl-2-[5-(1-methylsulfonylpiperidin-4-yl)pyridin-3-yl]isoindol-1-one

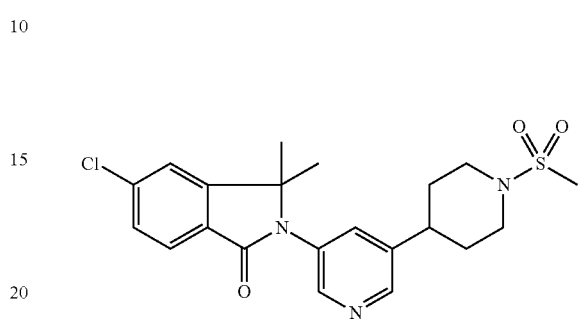

In analogy to the procedure described for the preparation of example 1, methane sulfonyl chloride (step A), 1-methanesulfonyl-1,2,3,6-tetrahydro-pyridine (step B), and 5-bromo-1'-methanesulfonyl-1',2',3',4',5',6'-hexahydro-[3,4']bipyridinyl (step C) were used to yield the title compound (26 mg) as a white solid. MS: 434.3 (M+H)$^+$.

Example 4

5-Chloro-2-[5-(1-ethylsulfonylpiperidin-3-yl)pyridin-3-yl]-3,3-dimethylisoindol-1-one

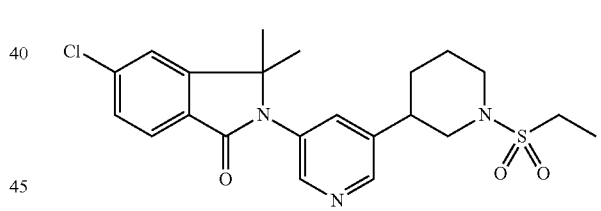

[A] 5'-Bromo-1-ethanesulfonyl-1,2,3,4,5,6-hexahydro-[3,3']bipyridinyl

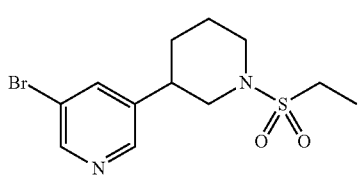 [SMILES: CCS(=O)(=O)N1CCCC(c2cncc(Br)c2)C1]

In analogy to the procedure described for the preparation of example 1[B], 1-ethanesulfonyl-1,2,3,6-tetrahydro-pyridine was used to yield the title compound as yellowish oil (250 mg) in a mixture with its regioisomer (ratio: ca 1:1). MS: 335.1 (M+H)$^+$.

[B] 5-Chloro-2-[5-(1-ethylsulfonylpiperidin-3-yl)pyridin-3-yl]-3,3-dimethylisoindol-1-one

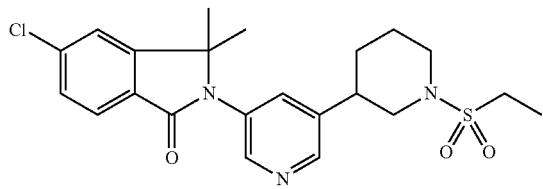 [SMILES: CCS(=O)(=O)N1CCCC(c2cncc(N3C(=O)c4ccc(Cl)cc4C3(C)C)c2)C1]

In analogy to the procedure described for the preparation of example 1[C], 5-bromo-1'-ethanesulfonyl-1',2',3',4',5',6'-hexahydro-[3,4']bipyridinyl was used to yield the title compound (8 mg) as a white solid. MS: 448.2 (M+H)$^+$.

Example 5 and Example 6

(+)-5-Chloro-3,3-dimethyl-2-[5-[(3R or 3S)-1-methylsulfonylpiperidin-3-yl]pyridin-3-yl]isoindol-1-one and (−)-5-chloro-3,3-dimethyl-2-[5-[(3S or 3R)-1-methylsulfonylpiperidin-3-yl]pyridin-3-yl]isoindol-1-one

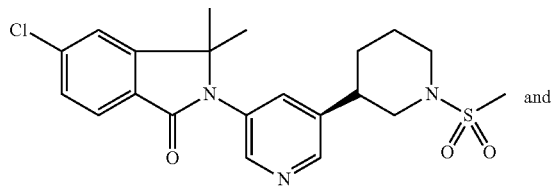

(+) - Example 5

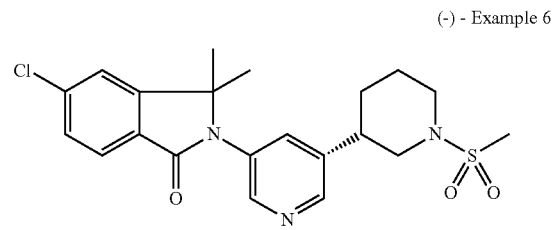

(−) - Example 6

An enantiomeric mixture of 5-chloro-3,3-dimethyl-2-[5-(1-methylsulfonylpiperidin-3-yl)pyridin-3-yl]isoindol-1-one (prepared in analogy to the procedures described for the preparation of example 4) was subject to SFC separation (AD 250 mm×30 mm, 20 um, mobile phase A: supercritical CO$_2$, B: EtOH (0.05% NH$_3$.H$_2$O), A:B=55:45 at 80 mL/min) to afford (+)-5-chloro-3,3-dimethyl-2-[5-[(3R or 3S)-1-methylsulfonylpiperidin-3-yl]pyridin-3-yl]isoindol-1-one (2.4 mg, example 5), MS: 434.2 (M+H)* and (−)-5-chloro-3,3-dimethyl-2-[5-[(3S or 3R)-1-methylsulfonylpiperidin-3-yl]pyridin-3-yl]isoindol-1-one (2 mg, example 6). MS: 434.2 (M+H)$^+$.

Example 7

5-Chloro-2-[5-(1-ethylsulfonylpyrrolidin-3-yl)pyridin-3-yl]-3,3-dimethylisoindol-1-one

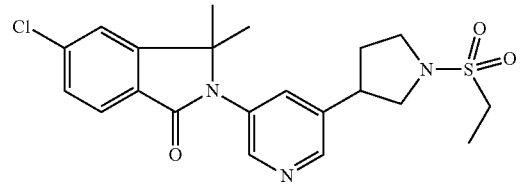 [SMILES: CCS(=O)(=O)N1CCC(c2cncc(N3C(=O)c4ccc(Cl)cc4C3(C)C)c2)C1]

[A] 3,5-Diiodo-pyridine

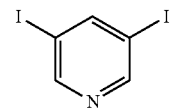

A mixture of 3,5-dibromo-pyridine (20 g, 84 mmol), CuI (4.76 g, 25 mmol), KI (83.7 g, 504 mmol) and N,N'-dimethyl-ethane-1,2-diamine (4.4 g, 50.4 mmol) in dioxane (400 mL) was stirred at 110° C. for 16 hours. The reaction solution was filtered and the filtrate was concentrated under reduced pressure to give a crude solid which was washed with EtOAc (100 mL) and DCM (100 mL) to give the title product as a white solid (13 g, 47%). MS: 331.5 (M+H)$^+$. It was used directly in the next step without further purification.

[B] 3-(5-Bromo-pyridin-3-yl)-pyrrolidine-1-carboxylic acid tert-butyl ester

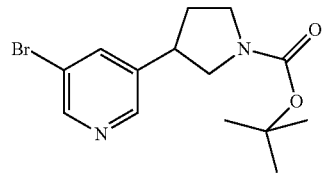 [SMILES: CC(C)(C)OC(=O)N1CCC(c2cncc(Br)c2)C1]

To a suspension of Zn dust (1.1 g, 16.6 mmol) in DMA (15 mL) was added a mixture of TMSCl and 1,2-dibromoethane (1.2 mL, 7:5). The mixture was stirred at 40° C. for 15 min before a solution of 3-iodo-pyrrolidine-1-carboxylic acid tert-butyl ester (4.5 g, 15.1 mmol) in DMA (15 mL) was added. After being stirred at room temperature for 2 hours, a mixture of 3,5-diiodo-pyridine (6 g, 18.1 mmol), CuI (435 mg, 2.3 mmol) and PdCl$_2$(dppf) (1.42 g, 1.8 mmol) was added and the resulting mixture was stirred at 90° C. for 16 hours. The reaction mixture was poured into water (200 mL), exacted with EtOAc (100 mL, 3×), washed with brine, dried over anhy. Na$_2$SO$_4$, and concentrated in vacuo to give a crude product which was purified by Pre-HPLC to give the title compound as a yellow solid (80 mg, 1.4%). MS: 327.2 (M+H)$^+$.

[C] 3-[5-(6-Chloro-1,1-dimethyl-3-oxo-1,3-dihydro-isoindol-2-yl)-pyridin-3-yl]-pyrrolidine-1-carboxylic acid tert-butyl ester

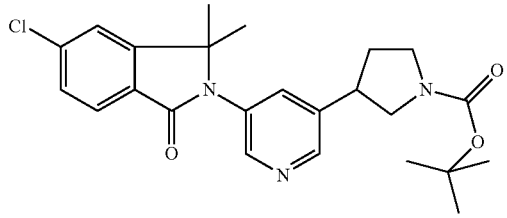 [SMILES: CC(C)(C)OC(=O)N1CCC(c2cncc(N3C(=O)c4ccc(Cl)cc4C3(C)C)c2)C1]

A mixture of 3-(5-bromo-pyridin-3-yl)-pyrrolidine-1-carboxylic acid tert-butyl ester (80 mg, 0.21 mmol), 5-chloro-3,3-dimethyl-2,3-dihydro-isoindol-1-one (49 mg, 0.25 mmol), N,N-dimethylbenzene-1,2-diamine (19 mg, 0.13 mmol), CuI (12 mg, 0.064 mmol) and $Cs_2CO_3$ (137 mg, 0.42 mmol) in dioxane (5 mL) was stirred at 150° C. under microwave for 2 hours. The resulting mixture was poured into water (50 mL) and the aqueous layer was exacted with EtOAc (30 mL, 3×). The combined organic layers were washed with brine, dried over anhy. $Na_2SO_4$, and concentrated in vacuo to give a crude title product (70 mg, 74%). It was used in the next step directly without further purification.

[D] 5-Chloro-2-[5-(1-ethylsulfonylpyrrolidin-3-yl)pyridin-3-yl]-3,3-dimethylisoindol-1-one

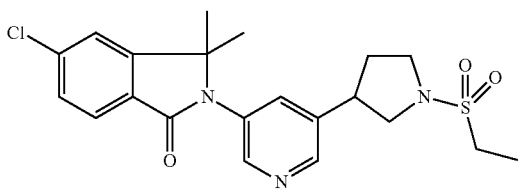 [SMILES: CCS(=O)(=O)N1CCC(c2cncc(N3C(=O)c4ccc(Cl)cc4C3(C)C)c2)C1]

A solution of 3-[5-(6-chloro-1,1-dimethyl-3-oxo-1,3-dihydro-isoindol-2-yl)-pyridin-3-yl]-pyrrolidine-1-carboxylic acid tert-butyl ester (70 mg, 0.16 mmol) and TFA (5 mL) in DCM (25 mL) was stirred at 0° C. for 2 hours. The reaction mixture was concentrated under reduced pressure before water (20 mL) was added. The pH was adjusted to 9 with aq. $Na_2CO_3$ solution and the mixture was exacted with DCM (30 mL, 3×). The combined organic layers were concentrated in vacuo to give an oil. This brown oil and TEA (32.3 mg, 0.32 mmol) in DCM (25 mL) was stirred at 0° C. before ethanesulfonyl chloride (41 mg, 0.32 mmol) was added. After being stirred for 30 min, the reaction solution was concentrated under reduced pressure to give a crude product which was purified by pre-HPLC to give the title compound (12 mg, 18%) as a white solid. MS: 433.8 (M+H)$^+$.

Example 8 and Example 9

(+)-5-Chloro-3,3-dimethyl-2-[5-[(3R or 3S)-1-propylsulfonylpyrrolidin-3-yl]pyridin-3-yl]isoindol-1-one and (−)-5-chloro-3,3-dimethyl-2-[5-[(3S or 3R)-1-propylsulfonylpyrrolidin-3-yl]pyridin-3-yl]isoindol-1-one

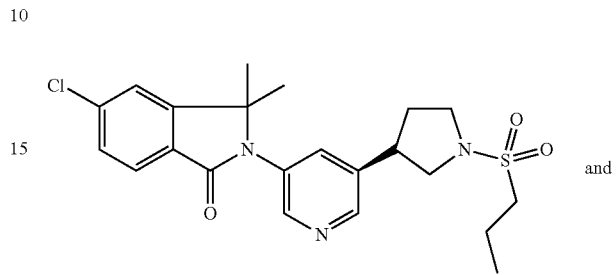

(+) - Example 8

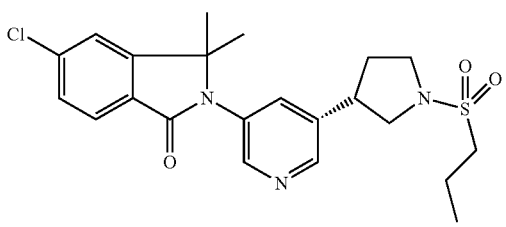

(−) - Example 9

[A] 3-(5-Bromo-pyridin-3-yl)-3-hydroxy-pyrrolidine-1-carboxylic acid tert-butyl ester

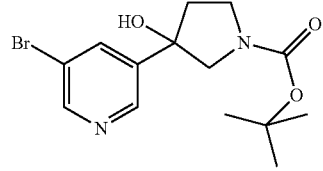 [SMILES: CC(C)(C)OC(=O)N1CCC(O)(c2cncc(Br)c2)C1]

To a stirring solution of 3,5-dibromo-pyridine (30 g, 0.13 mol) in $Et_2O$ (500 mL) was added n-BuLi (50 mL, 0.13 mol) at −78° C. under $N_2$. The mixture was stirred at −78° C. for 1 hour. Then the solution of 3-oxo-pyrrolidine-1-carboxylic acid tert-butyl ester (23.7 g, 0.13 mol) in $Et_2O$ (100 mL) was added at −78° C. and the mixture was allowed to warm up to room temperature and stirred for 3 hours. The reaction mixture was poured into water and extracted with EtOAc. The organic layer was washed with brine, dried over anhy. $Na_2SO_4$, filtered, and concentrated in vacuo. The residue was purified by silica gel column chromatography to afford the title compound (20 g, 44%) as a yellow solid. MS: 343.1 (M+H)$^+$.

[B] 3-(5-Bromo-pyridin-3-yl)-2,5-dihydro-pyrrole-1-carboxylic acid tert-butyl ester

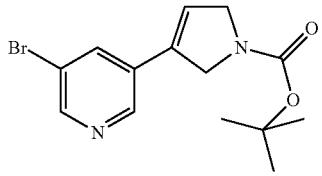 [SMILES: CC(C)(C)OC(=O)N1CC=C(c2cncc(Br)c2)C1]

To a solution of 3-(5-bromo-pyridin-3-yl)-3-hydroxy-pyrrolidine-1-carboxylic acid tert-butyl ester (15 g, 0.044 mol) in DCM was added Et$_3$N (8.9 g, 0.088 mol) and MsCl (15.1 g, 0.132 mol) at 0° C. The mixture was allowed to warm up to room temperature and stirred at room temperature overnight. The mixture was poured into ice water and extracted with DCM. The organic layer was washed with satd. aq. NH$_4$Cl solution, dried over anhy. Na$_2$SO$_4$, filtered, and concentrated in vacuo. The residue was purified by silica gel column chromatography to afford the title compound (10 g, 67%) as a yellow solid. MS: 325.1 (M+H)$^+$.

[C] 3-(5-Amino-pyridin-3-yl)-2,5-dihydro-pyrrole-1-carboxylic acid tert-butyl ester

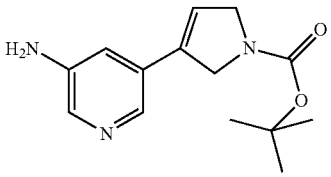 [SMILES: CC(C)(C)OC(=O)N1CC=C(c2cncc(N)c2)C1]

In a screw cap pressure tube, a mixture of CuI (0.1 g, 3 mmol), H-Hyp-OH (0.11 g, 0.62 mmol), and 3-(5-bromo-pyridin-3-yl)-2,5-dihydro-pyrrole-1-carboxylic acid tert-butyl ester (0.5 g, 1.5 mmol) in DMSO (25 mL) was added concentrated NH$_3$.H$_2$O (20 mL). It was heated at 80° C. overnight. After cooling to the room temperature, the reaction mixture was diluted with satd. aq. NH$_4$Cl solution and extracted with EtOAc. The organic layer was washed with water, dried over anhy. Na$_2$SO$_4$, filtered, and concentrated in vacuo to afford a crude title compound (0.35 g, 86%) as oil. MS: 261.3 (M+H)$^+$. It was used directly in the next step without further purification.

[D] 3-(5-Amino-pyridin-3-yl)-pyrrolidine-1-carboxylic acid tert-butyl ester

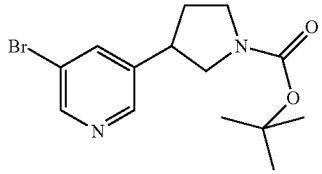

A solution of 3-(5-amino-pyridin-3-yl)-2,5-dihydro-pyrrole-1-carboxylic acid tert-butyl ester (0.3 g, 0.011 mol) in MeOH (10 mL) was treated with Pd/C (0.1 g). The flask was evacuated and backfilled with H$_2$ three times and stirred under H$_2$ atmosphere (50 psi) at 25° C. overnight. The mixture was filtered and concentrated to afford the title compound (0.3 g, quant.) as oil. MS: 264.2 (M+H$^+$). It was used directly in the next step without further purification.

[E] 3-(5-Bromo-pyridin-3-yl)-pyrrolidine-1-carboxylic acid tert-butyl ester

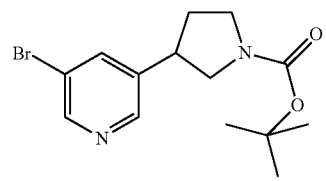 [SMILES: CC(C)(C)OC(=O)N1CCC(c2cncc(Br)c2)C1]

To a stirred solution of 3-(5-amino-pyridin-3-yl)-pyrrolidine-1-carboxylic acid tert-butyl ester in MeCN (50 mL) was added t-BuNO$_2$ (1.2 g, 9.4 mmol) at 0° C. The mixture was stirred at 0° C. for 1 hour before CuBr$_2$ (1.6 g, 7.2 mmol) was added and the mixture was allowed to warm up to room temperature and stirred overnight. The mixture was poured into brine, extracted with DCM. The organic layer was washed with water, dried over anhy. Na$_2$SO$_4$ and concentrated in vacuo. The residue was purified by silica gel column chromatography to afford the title compound (1.08 g, 48%) as a white solid. MS: 329.1 (M+H)$^+$.

[F] 3-[5-(6-Chloro-1,1-dimethyl-3-oxo-1,3-dihydro-isoindol-2-yl)-pyridin-3-yl]-pyrrolidine-1-carboxylic acid tert-butyl ester

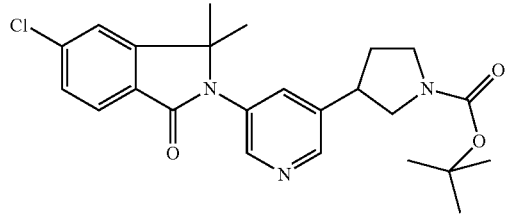 [SMILES: CC(C)(C)OC(=O)N1CCC(c2cncc(N3C(=O)c4ccc(Cl)cc4C3(C)C)c2)C1]

A mixture of 3-(5-bromo-pyridin-3-yl)-pyrrolidine-1-carboxylic acid tert-butyl ester (80 mg, 0.21 mmol), 5-chloro-3,3-dimethyl-2,3-dihydro-isoindol-1-one (49 mg, 0.25 mmol), N,N-dimethylbenzene-1,2-diamine (19 mg, 0.13 mmol), CuI (12 mg, 0.064 mmol) and Cs$_2$CO$_3$ (137 mg, 0.42 mmol) in dioxane (5 mL) was stirred at 150° C. under microwave for 2 hours. The resulting mixture was poured into water (50 mL). The aqueous layer was exacted with EtOAc (30 mL, 3×). The combined organic layers were washed with brine, dried over anhy. Na$_2$SO$_4$ and concentrated in vacuo to give a crude title product (70 mg, 74%) which was used directly in the next step without further purification.

[G] (+)-5-Chloro-3,3-dimethyl-2-[5-[(3R or 3S)-1-propylsulfonylpyrrolidin-3-yl]pyridin-3-yl]isoindol-1-one and (−)-5-chloro-3,3-dimethyl-2-[5-[(3S or 3R)-1-propylsulfonylpyrrolidin-3-yl]pyridin-3-yl]isoindol-1-one

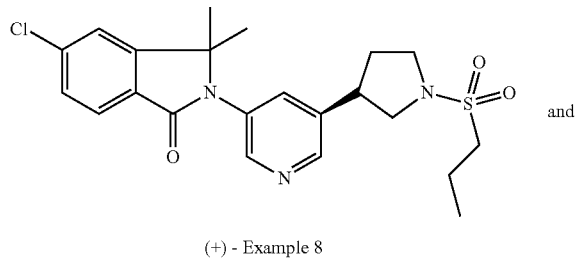

(+) - Example 8

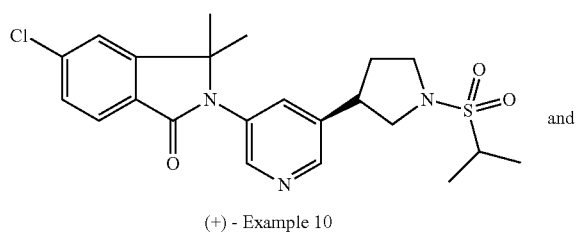

(−) - Example 9

In analogy to the procedure described for the preparation of example 7 (step D), propane-1-sulfonyl chloride was used to yield a racemic mixture of title compound (10 mg), which after SFC separation (column: chiralPak AD-H, 250×30 mm ID; mobile phase: A for $CO_2$ and B for methanol (0.1% $NH_3.H_2O$); gradient: 40% B; flow rate: 50 mL/min) affords (+)-5-chloro-3,3-dimethyl-2-[5-[(3R or 3S)-1-propylsulfonylpyrrolidin-3-yl]pyridin-3-yl]isoindol-1-one (2.9 mg, example 8), MS: 448.2 (M+H)+ and (−)-5-chloro-3,3-dimethyl-2-[5-[(3S or 3R)-1-propylsulfonylpyrrolidin-3-yl]pyridin-3-yl]isoindol-1-one (2.5 mg, example 9). MS: 448.2 (M+H)$^+$.

Example 10 and Example 11

(+)-5-Chloro-3,3-dimethyl-2-[5-[(3R or 3S)-1-propan-2-ylsulfonylpyrrolidin-3-yl]pyridin-3-yl]isoIndol-1-one and (−)-5-chloro-3,3-dimethyl-2-[5-[(3S or 3R)-1-propan-2-ylsulfonylpyrrolidin-3-yl]pyridin-3-yl]isoIndol-1-one

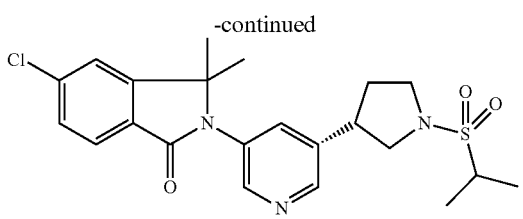

(+) - Example 10

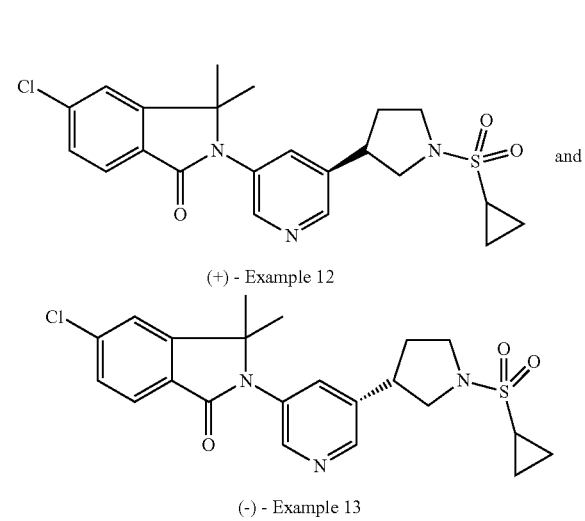

(−) - Example 11

In analogy to the procedure described for the preparation of example 7 (step D), propane-2-sulfonyl chloride was used to yield a racemic mixture of title compound (13 mg), which after SFC separation (column: chiralPak AD-H, 250×30 mm ID; mobile phase: A for $CO_2$ and B for methanol (0.1% $NH_3.H_2O$); gradient: 40% B; flow rate: 50 mL/min) affords the title compound (+)-5-chloro-3,3-dimethyl-2-[5-[(3R or 3S)-1-propan-2-ylsulfonylpyrrolidin-3-yl]pyridin-3-yl]isoindol-1-one (4 mg, example 10), MS: 448.1 (M+H)$^+$ and (−)-5-chloro-3,3-dimethyl-2-[5-[(3S or 3R)-1-propan-2-ylsulfonylpyrrolidin-3-yl]pyridin-3-yl]isoindol-1-one (3.1 mg, example 11). MS: 448.1 (M+H)$^+$.

Example 12 and Example 13

(+)-5-Chloro-2-[5-[(3R or 3S)-1-cyclopropylsulfonylpyrrolidin-3-yl]pyridin-3-yl]-3,3-dimethylisoindol-1-one and (−)-5-chloro-2-[5-[(3S or 3R)-1-cyclopropylsulfonylpyrrolidin-3-yl]pyridin-3-yl]-3,3-dimethylisondol-1-one In analogy to the procedure described for the preparation of example 7 (step D), cyclopropanesulfonyl chloride was used to yield a racemic mixture of title compound (17 mg), which after SFC separation (column: chiralPak AD-H, 250× 30 mm ID; mobile phase: A for $CO_2$ and B for methanol (0.1% NH3.$H_2O$); gradient: 40% B; flow rate: 50 mL/min) affords the title compound (+)-5-chloro-2-[5-[(3R or 3S)-1-cyclopropylsulfonylpyrrolidin-3-yl]pyridin-3-yl]-3,3-dimethylisoindol-1-one (4.7 mg, example 12), MS: 446.1 (M+H)$^+$ and (−)-5-chloro-2-[5-[(3S or 3R)-1-cyclopropylsulfonylpyrrolidin-3-yl]pyridin-3-yl]-3,3-dimethylisoindol-1-one (4.1 mg, example 13). MS: 446.1 (M+H)$^+$

Example 14

5-Chloro-2-[5-(3-fluoro-1-propan-2-ylsulfonylpyrrolidin-3-yl)pyridin-3-yl]-3,3-dimethylisoindol-1-one

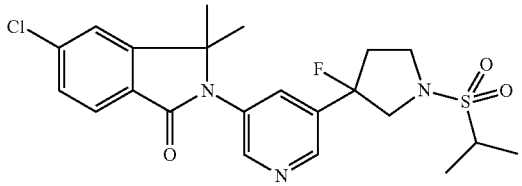 [SMILES: CC(C)S(=O)(=O)N1CCC(F)(c2cncc(N3C(=O)c4ccc(Cl)cc4C3(C)C)c2)C1]

[A] 3-(5-Bromo-pyridin-3-yl)-3-fluoro-pyrrolidine-1-carboxylic acid tert-butyl ester

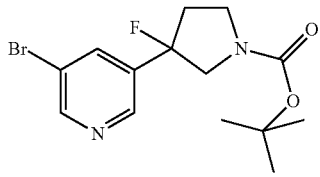 [SMILES: CC(C)(C)OC(=O)N1CCC(F)(c2cncc(Br)c2)C1]

Dast (1.3 g, 8 mmol) was added drop wise into a solution of 3-(5-bromo-pyridin-3-yl)-3-hydroxy-pyrrolidine-1-carboxylic acid tert-butyl ester (Example 8[A]) (1.37 g, 4 mmol) in DCM at 0° C. The reaction mixture was allowed to warm up to room temperature and stirred for 2 hours. After LC-MS and TLC shows the completion of starting material, aq. NaHCO₃ solution was slowly introduced into the reaction mixture. The separated organic layer was dried over anhy. Na₂SO₄ and concentrated in vacuo to give a crude residue which was purified by column chromotography (peter ether:EA=1:1) to give title compound (410 mg, 30%) as a yellow solid.

[B] 3-[5-(6-Chloro-1,1-dimethyl-3-oxo-1,3-dihydro-isoindol-2-yl)-pyridin-3-yl]-3-fluoro-pyrrolidine-1-carboxylic acid tert-butyl ester

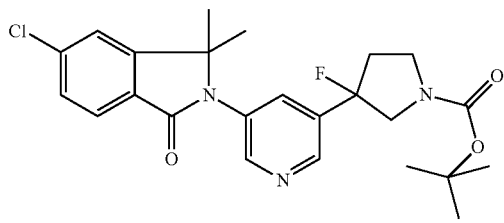 [SMILES: CC(C)(C)OC(=O)N1CCC(F)(c2cncc(N3C(=O)c4ccc(Cl)cc4C3(C)C)c2)C1]

In analogy to the procedure described for the preparation of example 7[C], 3-(5-bromo-pyridin-3-yl)-3-fluoro-pyrrolidine-1-carboxylic acid tert-butyl ester was used to yield the title compound as a crude product. It was used directly in the next step without further purification. MS: 345.1 (M+H)⁺.

[C] 5-Chloro-2-[5-(3-fluoro-1-propan-2-ylsulfonylpyrrolidin-3-yl)pyridin-3-yl]-3,3-dimethylisoindol-1-one

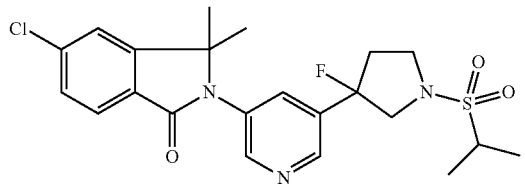 [SMILES: CC(C)S(=O)(=O)N1CCC(F)(c2cncc(N3C(=O)c4ccc(Cl)cc4C3(C)C)c2)C1]

In analogy to the procedure described for the preparation of example 7[D], propane-2-sulfonyl chloride was used to yield the tile compound as a white solid. MS: 466.2 (M+H)⁺.

Example 15

5-Chloro-3,3-dimethyl-2-[5-(1-propylsulfonylpiperidin-4-yl)pyridin-3-yl]isolndol-1-one

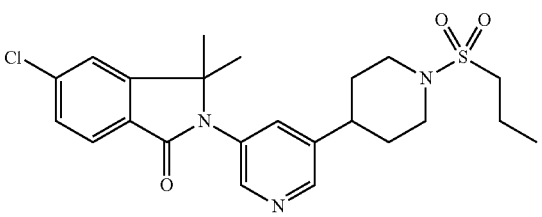 [SMILES: CCCS(=O)(=O)N1CCC(c2cncc(N3C(=O)c4ccc(Cl)cc4C3(C)C)c2)CC1]

[A] 5-Amino-3',6'-dihydro-2'H-[3,4']bipyridinyl-1'-carboxylic acid tert-butyl ester

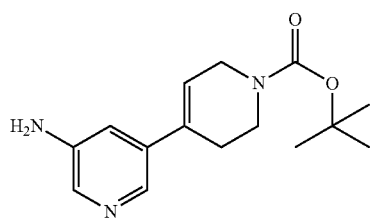 [SMILES: CC(C)(C)OC(=O)N1CC=C(c2cncc(N)c2)CC1]

A mixture of 5-bromopyridin-3-amine (5.5 g, 31.79 mmol), tert-butyl 4-(4,4,5,5-tetramethyl-1,3,2-dioxaborolan-2-yl)-5,6-dihydropyridine-1(2H)-carboxylate (9.83 g, 31.79 mmol), Pd(dppf)Cl₂ (1 g), Cs₂CO₃ (20.72 g) in dioxane (80 mL) and H₂O (2 mL) was heated at reflux temperature for 12 hours. After it was cooled to room temperature, the reaction mixture was diluted with EtOAc (300 mL) and the organic layer was washed with brine (80 mL, 2×), filtered, and concentrated in vacuo to give a crude product which was purified by chromatography (petroleum ether: ethyl acetate=10:1) to give title compound (7 g) as a yellow solid. MS: 276.5 (M+H)⁺.

[B] 5-Amino-3',4',5',6'-tetrahydro-2'H-[3,4']bipyridinyl-1'-carboxylic acid tert-butyl ester

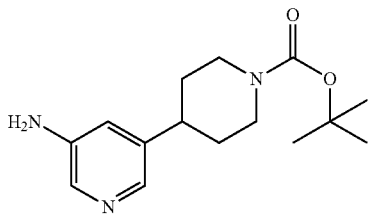 [SMILES: CC(C)(C)OC(=O)N1CCC(c2cncc(N)c2)CC1]

A mixture of tert-butyl 5-amino-5',6'-dihydro-[3,4'-bipyridine]-1'(2'H)-carboxylate (7 g, 25.4 mmol) and Pd/C (700 mg) in MeOH (50 mL) was stirred under 35 psi of H₂ at room temperature for 8 hours. After TLC (petroleum ether: EtOAc=3:1) showed full consumption of starting material, the mixture was filtered and the filtrate was concentrated in vacuo to give a crude product (7 g). It was used directly in the next step without further purification. MS: 278.0 (M+H)⁺.

[C] 5-Iodo-3',4',5',6'-tetrahydro-2'H-[3,4']bipyridinyl-1'-carboxylic acid tert-butyl ester

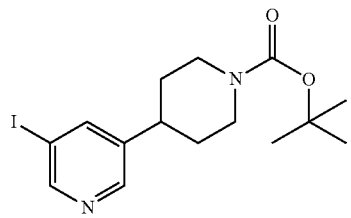 [SMILES: CC(C)(C)OC(=O)N1CCC(c2cncc(I)c2)CC1]

To a mixture of tert-butyl 4-(5-aminopyridin-3-yl) piperidine-1-carboxylate (7 g, 25.2 mmol) and p-TsOH (8.7 g, 50.48 mmol) in MeCN (100 mL) was added a solution of KI (6.28 g, 37.86 mmol) and NaNO₂ (2.61 g, 37.86 mmol) in water (20 mL) drop wise at −10° C. The mixture was stirred at 0° C. for 2 hours. After TLC (petroleum ether: EtOAc=3: 1) showed full consumption of starting material, the reaction mixture was diluted with EtOAc (300 mL) and basified with aq. NaHCO₃ solution to pH=8. The aqueous was extracted with EtOAc (300 mL, 3×), and the combined organic layers were washed with water (200 mL), brine (100 mL), dried over anhy. Na₂SO₄, filtered and concentrated in vacuo. The residue was purified by column chromatography (EA: petroleum ether=1:1) to give title compound (5.5 g) as a yellow solid. MS: 332.7 (M+H)⁺.

[D] 5-(6-Chloro-1,1-dimethyl-3-oxo-1,3-dihydro-isoindol-2-yl)-3',4',5',6'-tetrahydro-2'H-[3,4']bipyridinyl-1'-carboxylic acid tert-butyl ester

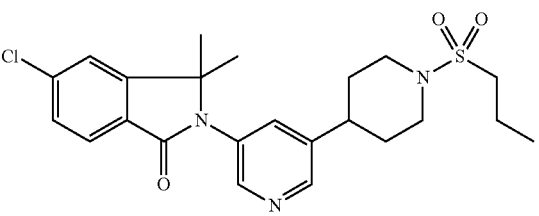 [SMILES: CCCS(=O)(=O)N1CCC(c2cncc(N3C(=O)c4ccc(Cl)cc4C3(C)C)c2)CC1]

In analogy to the procedure described for the preparation of example 7[C], 5-iodo-3',4',5',6'-tetrahydro-2'H-[3,4']bipyridinyl-1'-carboxylic acid tert-butyl ester was used to yield the title compound as a crude product. It was used directly in the next step without further purification. MS: 456.1 (M+H)⁺.

[E] 5-Chloro-3,3-dimethyl-2-[5-(1-propylsulfonylpiperidin-4-yl)pyridin-3-yl]isoindol-1-one In analogy to the procedure described for the preparation of example 7[D], propane-1-sulfonyl chloride was used to yield the title compound as a white solid. MS: 462.1 (M+H)⁺

The following examples listed in Table 1 were prepared in analogy to the procedures described for the preparation of example 15 using appropriate starting materials:

TABLE 1

| Ex | Name | Reactant | MS (M + H⁺) |
|---|---|---|---|
| 16 | 5-Chloro-3,3-dimethyl-2-[5-(1-propan-2-ylsulfonylpiperidin-4-yl)pyridin-3-yl]isoindol-1-one | 5-(6-Chloro-1,1-dimethyl-3-oxo-1,3-dihydro-isoindol-2-yl)-3',4',5',6'-tetrahydro-2'H-[3,4']bipyridinyl-1'-carboxylic acid tert-butyl ester (Example A-15[D]) and propane-2-sulfonyl chloride | 462.1 |

TABLE 1-continued

| Ex | Name | Reactant | MS (M + H⁺) |
|---|---|---|---|
| 17 | 5-Chloro-2-[5-(1-cyclopropylsulfonylpiperidin-4-yl)pyridin-3-yl]-3,3-dimethylisoindol-1-one | 5-(6-Chloro-1,1-dimethyl-3-oxo-1,3-dihydro-isoindol-2-yl)-3',4',5',6'-tetrahydro-2'H-[3,4']bipyridinyl-1'-carboxylic acid tert-butyl ester (Example A-15[D]) and cyclopropane-sulfonyl chloride | 460.1 |
| 18 | 5-Chloro-3,3-dimethyl-2-[5-[1-(4-methylpyridine-3-carbonyl)piperidin-4-yl]pyridin-3-yl]isoindol-1-one | 5-(6-Chloro-1,1-dimethyl-3-oxo-1,3-dihydro-isoindol-2-yl)-3',4',5',6'-tetrahydro-2'H-[3,4']bipyridinyl-1'-carboxylic acid tert-butyl ester (Example A-15[D]) and 4-methyl-nicotinoyl chloride | 475.2 |
| 19 | 5-Chloro-2-[5-[1-(3-chloropyridine-4-carbonyl)piperidin-4-yl]pyridin-3-yl]-3,3-dimethylisoindol-1-one | 5-(6-Chloro-1,1-dimethyl-3-oxo-1,3-dihydro-isoindol-2-yl)-3',4',5',6'-tetrahydro-2'H-[3,4']bipyridinyl-1'-carboxylic acid tert-butyl ester (Example A-15[D]) and 3-chloro-isonicotinoyl chloride | 495.1 |
| 20 | 5-Chloro-2-[5-[1-(3-chloropyridine-2-carbonyl)piperidin-4-yl]pyridin-3-yl]-3,3-dimethylisoindol-1-one | 5-(6-Chloro-1,1-dimethyl-3-oxo-1,3-dihydro-isoindol-2-yl)-3',4',5',6'-tetrahydro-2'H-[3,4']bipyridinyl-1'-carboxylic acid tert-butyl ester (Example A-15[D]) and 3-chloro-pyridine-2-carbonyl chloride | 495.2 |

Example 21

5-Chloro-2-[5-(1-ethylsulfonylpiperidin-4-yl)pyridin-3-yl]-3H-isoindol-1-one

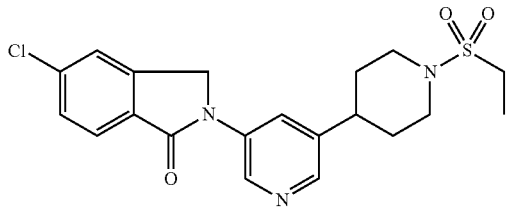 [SMILES: CCS(=O)(=O)N1CCC(c2cncc(N3Cc4cc(Cl)ccc4C3=O)c2)CC1]

[A] 5-(5-Chloro-1-oxo-1,3-dihydro-isoindol-2-yl)-3',4',5',6'-tetrahydro-2'H-[3,4']bipyridinyl-1'-carboxylic acid tert-butyl ester

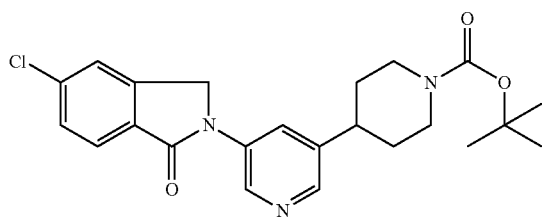 [SMILES: CC(C)(C)OC(=O)N1CCC(c2cncc(N3Cc4cc(Cl)ccc4C3=O)c2)CC1]

A mixture of 5-chloro-2,3-dihydro-isoindol-1-one (71 mg, 0.43 mmol), 5-iodo-3',4',5',6'-tetrahydro-2'H-[3,4']bipyridinyl-1'-carboxylic acid tert-butyl ester (150 mg, 0.38 mmol) (example 15[C]), CuI (22 mg, 0.11 mmol), (1S,2S)-cyclohexane-1,2-diamine (0.03 mL, 0.22 mmol) and $K_3PO_4$ (165 mg, 0.77 mmol) in dioxane (10 mL) was stirred at 120° C. for 2 hours. The resulting mixture was poured into water (50 mL) and the aqueous was exacted with EtOAc (30 mL, 3×). The combined organic layers were washed with brine, dried over anhy. $Na_2SO_4$ and concentrated in vacuo to get a crude product which was purified by column chromatography (EtOAc: PE=1:1) to afford title compound (100 mg, 61%) as a yellow foam. MS: 428.1 $(M+H)^+$.

[B] 5-Chloro-2-(1',2',3',4',5',6'-hexahydro-[3,4']bipyridinyl-5-yl)-2,3-dihydro-isoindol-1-one

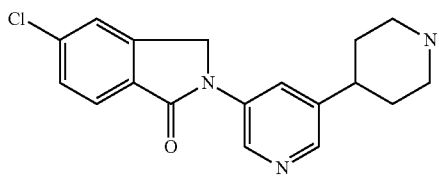 [SMILES: O=C1c2ccc(Cl)cc2CN1c1cncc(C2CCNCC2)c1]

A mixture of 5-(5-chloro-1-oxo-1,3-dihydro-isoindol-2-yl)-3',4',5',6'-tetrahydro-2'H-[3,4']bipyridinyl-1'-carboxylic acid tert-butyl ester (100 mg) and acetyl chloride (0.56 mL) in methanol (12 mL) was stirred at room temperature for 2 hours. After concentration in vacuo, it gave a crude product which was used without further purification as a light yellow foam. MS: 328.1 $(M+H)^+$.

[C] 5-Chloro-2-[5-(1-ethylsulfonylpiperidin-4-ylpyridin-3-yl]-3H-isoindol-1-one

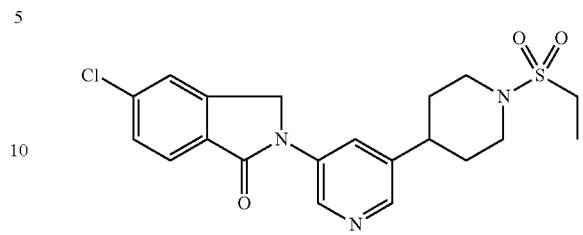

To a stirred brown solution of 5-chloro-2-(1',2',3',4',5',6'-hexahydro-[3,4']bipyridinyl-5-yl)-2,3-dihydro-isoindol-1-one (33 mg, 0.1 mmol) and $Et_3N$ (0.50 mL) in DCM (5 mL) was added ethanesulfonyl chloride (0.014 mL, 0.13 mmol) at 0° C. and the mixture was stirred at 0° C. for 1 hour. The resulting mixture was extracted with EtOAc (2×50 mL) and the combined organics were washed with brine, dried over anhy. $Na_2SO_4$, filtered and concentrated in vacuo. The residue was purified by Pre-HPLC to afford title compound (18 mg, 43%) as white foam. MS: 420.1 $(M+H)^+$.

Example 22

5-Chloro-2-[5-(1-propan-2-ylsulfonylpiperdin-4-yl)pyridin-3-yl]-3H-isolndol-1-one

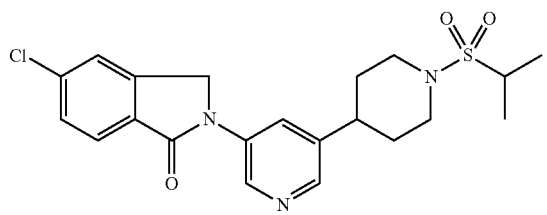 [SMILES: CC(C)S(=O)(=O)N1CCC(c2cncc(N3Cc4cc(Cl)ccc4C3=O)c2)CC1]

In analogy to the procedure described for the preparation of example 21 [C], propane-2-sulfonyl chloride was used to yield the tile compound as a white solid. MS: 434.1 $(M+H)^+$.

Example 23

5-Chloro-2-[5-[1-(4-methylpyridine-3-carbonyl)piperidin-4-yl]pyridin-3-yl]-3H-Isolndol-1-one

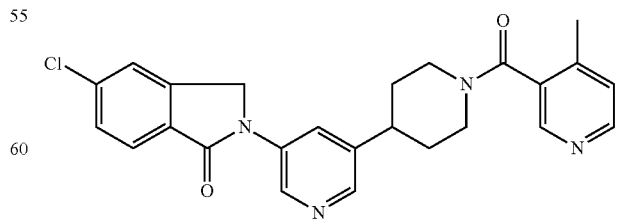

In analogy to the procedure described for the preparation of example 21 [C], 4-methyl-nicotinoyl chloride was used to yield the tile compound as a white solid. MS: 447.1 $(M+H)^+$.

Example 24 and Example 25

(+)-(3R or 3S)-5-Chloro-2-[5-(1-ethylsulfonylpiperidin-4-yl)pyridin-3-yl]-3-methyl-3H-isoindol-1-one and (−)-(3S or 3R)-5-chloro-2-[5-(1-ethylsulfonylpiperidin-4-yl)pyridin-3-yl]-3-methyl-3H-isoindol-1-one

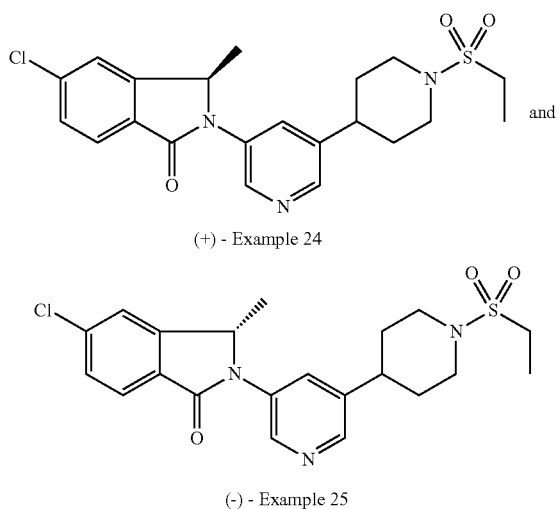

(+) - Example 24

(−) - Example 25

In analogy to the procedure described for the preparation of example 21, 5-chloro-3-methyl-2,3-dihydro-isoindol-1-one (intermediate A-2) (step A) and ethanesulfonyl chloride (step C) were used to yield the title compound as a crude racemic mixture (50 mg), which after SFC separation (IC 250 mm×50 mm, 5 um, mobile phase A: supercritical CO$_2$, B: ethanol (0.05% NH$_3$.H$_2$O), A:B=50:50 at 2 mL/min) affords (+)-(3R or 3S)-5-chloro-2-[5-(1-ethylsulfonylpiperidin-4-yl)pyridin-3-yl]-3-methyl-3H-isoindol-1-one (12 mg, example 24) as off-white foam, MS: 434.1 (M+H)$^+$ and (−)-(3S or 3R)-5-chloro-2-[5-(1-ethylsulfonylpiperidin-4-yl)pyridin-3-yl]-3-methyl-3H-isoindol-1-one (15 mg, example 25) as off-white foam. MS: 434.1 (M+H)$^+$.

Example 26 and Example 27

(+)-(3R or 3S)-5-Chloro-3-methyl-2-[5-(1-propan-2-ylsulfonylpiperidin-4-yl)pyridin-3-yl]-3H-isoindol-1-one and (−)-(3S or 3R)-5-chloro-3-methyl-2-[5-(1-propan-2-ylsulfonylpiperidin-4-yl)pyridin-3-yl]-3H-isolndol-1-one

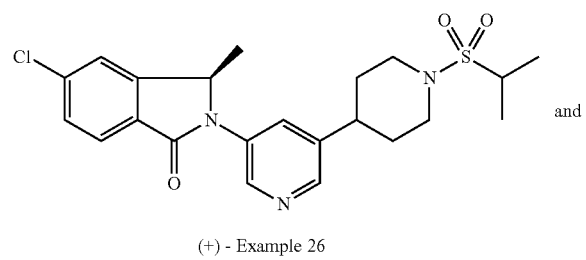

(+) - Example 26

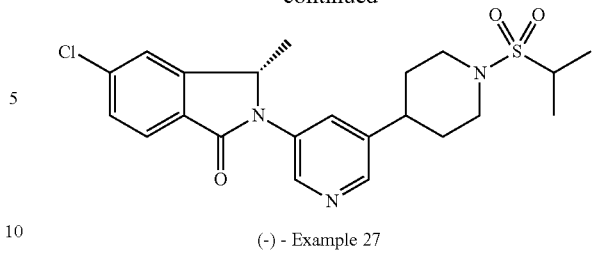

(−) - Example 27

In analogy to the procedure described for the preparation of example 21, 5-chloro-3-methyl-2,3-dihydro-isoindol-1-one (intermediate A-2) (step A) and propane-2-sulfonyl chloride (step C) were used to yield the title compound as a crude racemic mixture (20 mg), which after SFC separation (IC 250 mm×50 mm, 5 um, mobile phase A: supercritical CO$_2$, B: ethanol (0.05% NH$_3$.H$_2$O), A:B=50:50 at 2 mL/min) affords (+)-(3R or 3S)-5-chloro-3-methyl-2-[5-(1-propan-2-ylsulfonylpiperidin-4-yl)pyridin-3-yl]-3H-isoindol-1-one (4 mg, example 26) as off-white foam, MS: 448.1 (M+H)$^+$ and (−)-(3S or 3R)-5-chloro-3-methyl-2-[5-(1-propan-2-ylsulfonylpiperidin-4-yl)pyridin-3-yl]-3H-isoindol-1-one (5 mg, example 27) as off-white foam. MS: 448.1 (M+H)$^+$.

Example 28 and Example 29

(+)-3R or 3S)-5-Chloro-3-methyl-2-[5-[1-(4-methylpyridine-3-carbonyl)piperidin-4-yl]pyridin-3-yl]-3H-isoindol-1-one and (−)-(3S or 3R)-5-chloro-3-methyl-2-[5-[1-(4-methylpyridine-3-carbonyl)piperidin-4-yl]pyridin-3-yl]-3H-isoindol-1-one

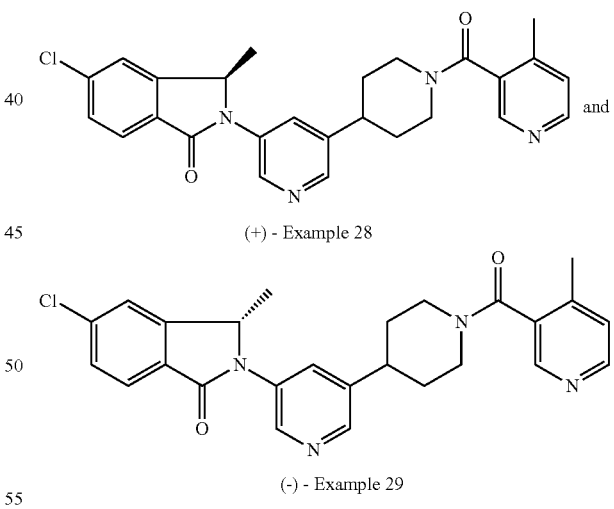

(+) - Example 28

(−) - Example 29

In analogy to the procedure described for the preparation of example 21, 5-chloro-3-methyl-2,3-dihydro-isoindol-1-one (intermediate A-2) (step A) and 4-methyl-nicotinoyl chloride (step C) were used to yield the title compound as a crude racemic mixture (50 mg), which after SFC separation (IC 250 mm×50 mm, 5 um, mobile phase A: supercritical CO$_2$, B: ethanol (0.05% NH$_3$.H$_2$O), A:B=50:50 at 2 mL/min) affords (+)-(3R or 3S)-5-chloro-3-methyl-2-[5-[1-(4-methylpyridine-3-carbonyl)piperidin-4-yl]pyridin-3-yl]-3H-isoindol-1-one (13 mg, example 28) as off-yellow foam, MS: 461.1 (M+H)$^+$ and (−)-(3S or 3R)-5-chloro-3-methyl- 2-[5-[1-(4-methylpyridine-3-carbonyl)piperidin-4-yl]pyridin-3-yl]-3H-isoindol-1-one (17 mg, example 29) as off-yellow foam. MS: 461.1 (M+H)+.

Example 30

5-Chloro-2-[5-(1-ethylsulfonyl-4-fluoropiperidin-4-yl)pyridin-3-yl]-3,3-dimethylisoindol-1-one

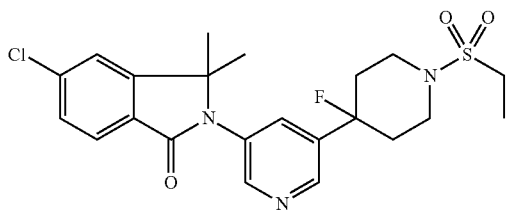 [SMILES: CCS(=O)(=O)N1CCC(F)(c2cncc(N3C(=O)c4ccc(Cl)cc4C3(C)C)c2)CC1]

[A] 5-Bromo-4'-hydroxy-3',4',5',6'-tetrahydro-2'H-[3,4']bipyridinyl-1'-carboxylic acid tert-butyl ester

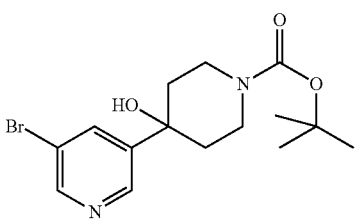 [SMILES: CC(C)(C)OC(=O)N1CCC(O)(c2cncc(Br)c2)CC1]

In analogy to the procedure described for the preparation of example 8[A], 4-oxo-piperidine-1-carboxylic acid tert-butyl ester was used to yield the title compound (2 g, 56%) as a white solid. MS: 357.0 (M+H)

[B] 5-Bromo-4'-fluoro-3',4',5',6'-tetrahdro-2'H-[3,4']bipyridinyl-1'-carboxylic acid tert-butyl ester

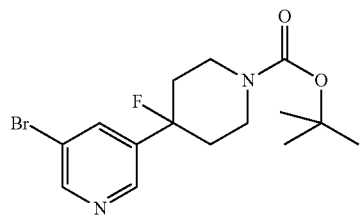 [SMILES: CC(C)(C)OC(=O)N1CCC(F)(c2cncc(Br)c2)CC1]

In analogy to the procedure described for the preparation of example 14[A], 5-bromo-4'-hydroxy-3',4',5',6'-tetrahydro-2'H-[3,4]bipyridinyl-1'-carboxylic acid tert-butyl ester was used to yield the title compound (500 mg, 48%) as a white solid. MS: 359.1 (M+H)+

[C] 5-(6-Chloro-1,1-dimethyl-3-oxo-1,3-dihydro-isoindol-2-yl)-4'-fluoro-3',4',5',6'-tetrahydro-2'H-[3,4']bipyridinyl-1'-carboxylic acid tert-butyl ester

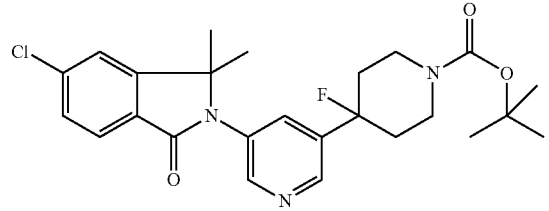 [SMILES: CC(C)(C)OC(=O)N1CCC(F)(c2cncc(N3C(=O)c4ccc(Cl)cc4C3(C)C)c2)CC1]

In analogy to the procedure described for the preparation of example 7[C], 5-bromo-4'-fluoro-3',4',5',6'-tetrahydro-2'H-[3,4']bipyridinyl-1'-carboxylic acid tert-butyl ester was used to yield the title compound as a crude product. It was used directly in the next step without further purification. MS: 474.1 (M+H)+.

[D] 5-Chloro-2-[5-(1-ethylsulfonyl-4-fluoropiperidin-4-yl)pyridin-3-yl]-3,3-dimethylisoindol-1-one

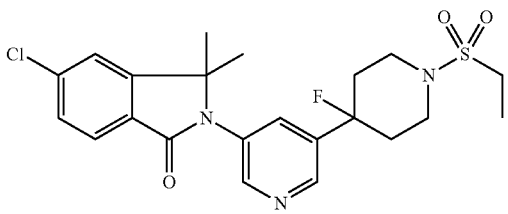 [SMILES: CCS(=O)(=O)N1CCC(F)(c2cncc(N3C(=O)c4ccc(Cl)cc4C3(C)C)c2)CC1]

In analogy to the procedure described for the preparation of example 7[D], ethanesulfonyl chloride was used to yield the title compound (6 mg) as a white solid. MS: 466.2 (M+H)+.

Example 31

5-Chloro-2-[5-(4-fluoro-1-propan-2-ylsulfonylpiperidin-4-yl)pyrdin-3-yl]-3,3-dimethylisoindol-1-one

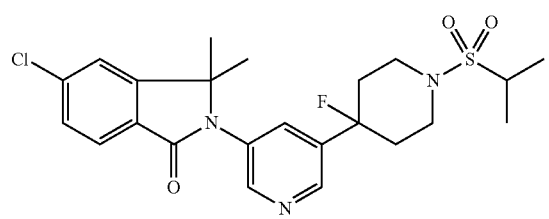 [SMILES: CC(C)S(=O)(=O)N1CCC(F)(c2cncc(N3C(=O)c4ccc(Cl)cc4C3(C)C)c2)CC1]

In analogy to the procedure described for the preparation of example 30[D], propane-2-sulfonyl chloride was used to yield the title compound (6 mg) as a white solid. MS: 480.2 (M+H)+.

Example 32

5-Chloro-2-[5-(1-ethylsulfonylazetidin-3-yl)pyridin-3-yl]-3,3-dimethylisoindol-1-one

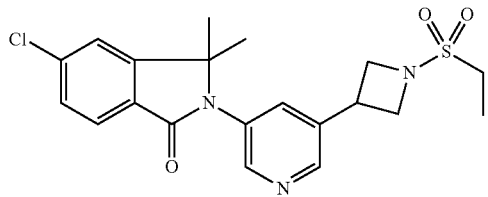 [SMILES: CCS(=O)(=O)N1CC(c2cncc(N3C(=O)c4ccc(Cl)cc4C3(C)C)c2)C1]

[A] 5-Chloro-2-(5-iodo-pyridin-3-yl)-3,3-dimethyl-2,3-dihydro-isoindol-1-one

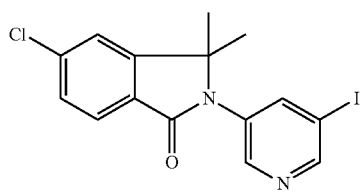 [SMILES: CC1(C)c2cc(Cl)ccc2C(=O)N1c1cncc(I)c1]

A mixture of 5-chloro-3,3-dimethyl-2,3-dihydro-isoindol-1-one (intermediate A-3) (2.3 g, 11.8 mmol), 3,5-diiodo-pyridine (example 7[A]) (6.9 g, 21 mmol), CuI (673 mg, 3.54 mmol), $K_3PO_4$ (5.0 g, 23.6 mmol) and trans-cyclohexane-1,2-diamine (810 mg, 7.1 mmol) in dioxane (50 mL) was stirred at 110° C. for 2 hours. The reaction was filtered and the filtrate was concentrated under reduced pressure to give a crude solid which was purified by flash chromatography to give the title product as a white solid (1.7 g, 36%). MS: 398.7 (M+H)$^+$.

[B] 5-Chloro-3,3-dimethyl-2-[5-(4,4,5,5-tetramethyl-[1,3,2]dioxaborolan-2-yl)-pyridin-3-yl]-2,3-dihydro-isoindol-1-one

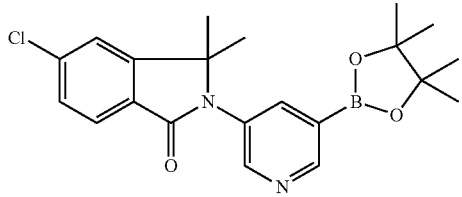 [SMILES: CC1(C)c2cc(Cl)ccc2C(=O)N1c1cncc(B2OC(C)(C)C(C)(C)O2)c1]

A mixture of 5-chloro-2-(5-iodo-pyridin-3-yl)-3,3-dimethyl-2,3-dihydro-isoindol-1-one (200 mg, 0.5 mmol), 4,4,4',4',5,5,5',5'-octamethyl-2,2'-bi(1,3,2-dioxaborolane) (153 mg, 0.6 mmol), KOAc (98 mg, 1.0 mmol) in 1,4-dioxane (1 mL) and DMSO (5 mL) was purged with nitrogen for 10 min before [1,1'-bis(diphenylphosphino)ferrocene]-dichloropalladium DCM adduct (11 mg, 0.015 mmol) was added. The mixture was purged with nitrogen for another 5 min and then heated at reflux for 2 hours. After cooling to room temperature, the mixture was washed with ether and brine, and the organic layer was dried over anhy. $Na_2SO_4$ and concentrated in vacuo to afford a crude product as yellowish oil. It was used directly in the next step without further purification. MS: 339.0 (M+H)$^+$.

[C] 3-[5-(6-Chloro-1,1-dimethyl-3-oxo-1,3-dihydro-isoindol-2-yl)-pyridin-3-yl]-azetidine-1-carboxylic acid tert-butyl ester

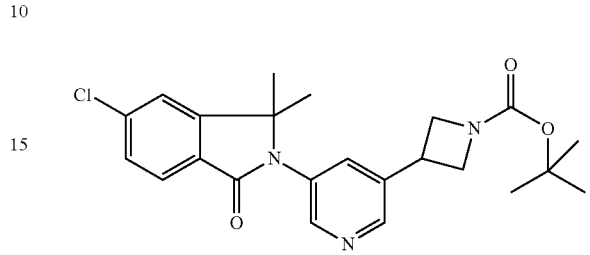

A mixture of 5-chloro-3,3-dimethyl-2-[5-(4,4,5,5-tetramethyl-[1,3,2]dioxaborolan-2-yl)-pyridin-3-yl]-2,3-dihydro-isoindol-1-one (170 mg, 0.5 mmol), $NiI_2$ (5 mg, 0.015 mmol), trans-2-aminocyclohexanol hydrochloride (3 mg, 0.015 mmol) and NaHMDS (92 mg, 0.5 mmol) in dry iPrOH (5 mL) was stirred at room temperature under $N_2$ for 5 min. A solution of 3-iodo-azetidine-1-carboxylic acid tert-butyl ester (141 mg, 0.5 mmol) in dry iPrOH (1 mL) was added and the resulting mixture was heated to 80° C. under microwave irradiation for 30 min. The reaction solution was concentrated under reduced pressure to give a crude mixture which was purified by flash chromatography to give the title product as light yellowish oil (15 mg, 7% over two steps). MS: 428.3 (M+H)$^+$.

[D] 5-Chloro-2-[5-(1-ethylsulfonylazetidin-3-yl)pyridin-3-yl]-3,3-dimethylisoindol-1-one

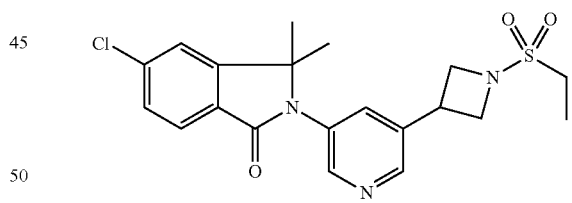

To a solution of 3-[5-(6-chloro-1,1-dimethyl-3-oxo-1,3-dihydro-isoindol-2-yl)-pyridin-3-yl]-azetidine-1-carboxylic acid tert-butyl ester (15 mg, 0.04 mmol) in MeOH (7 mL) was added AcCl (58 mg, 1 mmol) at 0° C. and the reaction mixture was stirred at room temperature for 1 hour. The solution was concentrated in vacuo to give yellowish oil. After being dried in high vacuo for 2 hours, it was used directly in the next step. The yellowish oil and TEA (1 g, 10 mmol) in DCM (25 mL) was stirred at 0° C. and ethanesulfonyl chloride (64 mg, 0.5 mmol) was added. After being stirred for overnight, the reaction solution was concentrated under reduced pressure. The residue was purified by prep-HPLC to give the title product (2.7 mg) as a white solid. MS: 420.2 (M+H)$^+$.

Example 33

2-[5-(1-Acetylazetidin-3-yl)pyridin-3-yl]-5-chloro-3,3-dimethylisoindol-1-one

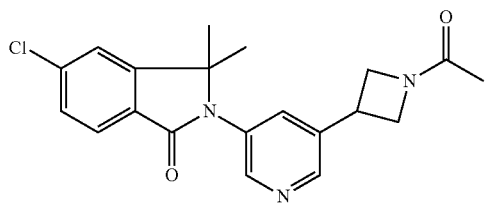 [SMILES: CC(=O)N1CC(c2cncc(N3C(=O)c4ccc(Cl)cc4C3(C)C)c2)C1]

[A] 3-(5-Bromo-pyridin-3-yl)-azetidine-1-carboxylic acid tert-butyl ester

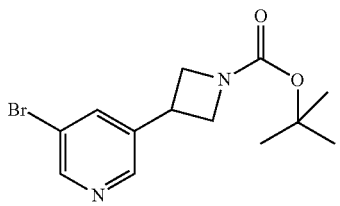 [SMILES: CC(C)(C)OC(=O)N1CC(c2cncc(Br)c2)C1]

A mixture of 3-bromo-5-(4,4,5,5-tetramethyl-[1,3,2]dioxaborolan-2-yl)-pyridine (1.18 g, 5.8 mmol), NiI$_2$ (200 mg, 0.64 mmol), trans-2-aminocyclohexanol hydrochloride (100 mg, 0.66 mmol) and NaHMDS (2.2 g, 12 mmol) in dry iPrOH (10 mL) was stirred at room temperature under N$_2$ for 5 min. A solution of 3-iodo-azetidine-1-carboxylic acid tert-butyl ester (1.6 g, 8.8 mmol) in dry iPrOH (1 mL) was then added. The resulting mixture was heated to 80° C. under microwave irradiation for 50 min. The reaction solution was concentrated under reduced pressure to give a brown mixture which was purified by flash chromatography to give the title product as colorless oil (400 mg, 22%). MS: 313.1 (M+H)$^+$.

[B] 3-[5-(6-Chloro-1,1-dimethyl-3-oxo-1,3-dihydro-isoindol-2-yl)-pyridin-3-yl]-azetidine-1-carboxylic acid tert-butyl ester

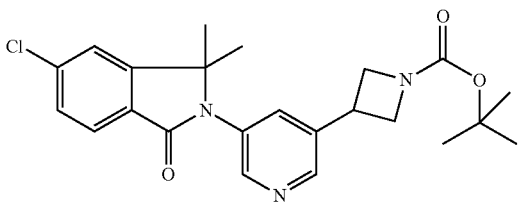 [SMILES: CC(C)(C)OC(=O)N1CC(c2cncc(N3C(=O)c4ccc(Cl)cc4C3(C)C)c2)C1]

A mixture of 3-(5-bromo-pyridin-3-yl)-azetidine-1-carboxylic acid tert-butyl ester (400 mg, 1.3 mmol), 5-chloro-3,3-dimethyl-2,3-dihydro-isoindol-1-one (396 mg, 2 mmol), CuI (100 mg, 0.52 mmol), Cs$_2$CO$_3$ (700 mg, 2 mmol) and trans-cyclohexane-1,2-diamine (100 mg, 0.88 mmol) in dioxane (5 mL) was stirred at 110° C. overnight. The solution was filtered and the filtrate was concentrated under reduced pressure to give a crude solid which was purified by flash chromatography to give the title product as light yellowish oil (100 mg, 19%). MS: 428.3 (M+H).

[C] 2-(5-Azetidin-3-yl-pyridin-3-yl)-5-chloro-3,3-dimethyl-2,3-dihydro-isoindol-1-one hydrochloride

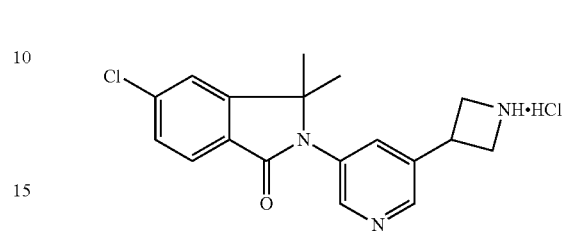

To a solution of 3-[5-(6-chloro-1,1-dimethyl-3-oxo-1,3-dihydro-isoindol-2-yl)-pyridin-3-yl]-azetidine-1-carboxylic acid tert-butyl ester (140 mg, 0.33 mmol) in MeOH (10 mL) was added AcCl (5 mL, 7.1 mmol) at 0° C. and the mixture was then stirred at room temperature for 1 hour. The reaction solution was concentrated in vacuo to give yellowish oil which was dried in high vacuo for 2 hours. It was used directly in the next step without further purification. MS: 328.2 (M+H)$^+$.

[D] 2-[5-(1-Acetylazetidin-3-yl)pyridin-3-yl]-5-chloro-3,3-dimethylisoindol-1-one

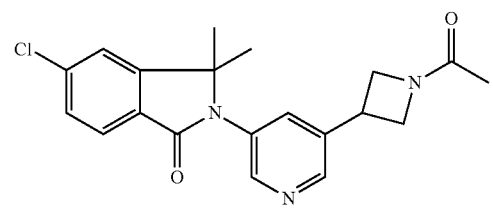

To a solution of 2-(5-azetidin-3-yl-pyridin-3-yl)-5-chloro-3,3-dimethyl-2,3-dihydro-isoindol-1-one hydrochloride (35 mg, 0.096 mmol) and TEA (101 mg, 1 mmol) in DCM (5 mL) at 0° C. was added AcCl (30 mg, 0.38 mmol). After being stirred for 30 min at 0° C., the reaction solution was concentrated under reduced pressure. The residue was purified by prep-HPLC to give the title product (4.8 mg) as a white solid. MS: 370.2 (M+H)$^+$.

Example 34

5-Chloro-3,3-dimethyl-2-[5-(1-propylsulfonylazetldin-3-yl)pyridin-3-yl]isolndol-1-one

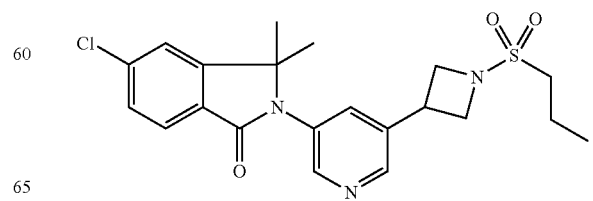

In analogy to the procedure for the preparation of example 33, propane-1-sulfonyl chloride was used to give title compound (5.1 mg) as a white solid. MS: 434.2 (M+H)+.

Example 35

5-Chloro-2-[5-(1-cyclopropylsulfonylazetldin-3-yl)pyridin-3-yl]-3,3-dimethylisoindol-1-one

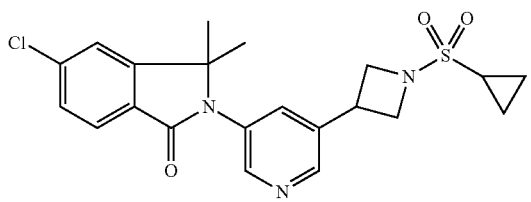 [SMILES: CC1(C)c2cc(Cl)ccc2C(=O)N1c1cncc(C2CN(S(=O)(=O)C3CC3)C2)c1]

In analogy to the procedure for the preparation of example 33, cyclopropanesulfonyl chloride was used to give title compound (19.4 mg) as a white solid. MS: 432.2 (M+H)+.

Example 36

5-Chloro-3,3-dimethyl-2-[5-[1-(4-methylpyridine-3-carbonyl)azetidin-3-yl]pyridin-3-yl]isolndol-1-one

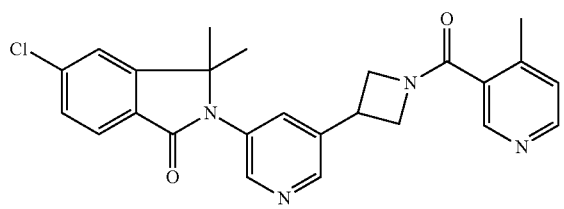 [SMILES: Cc1ccncc1C(=O)N1CC(c2cncc(N3C(=O)c4ccc(Cl)cc4C3(C)C)c2)C1]

To a solution of 2-(5-azetidin-3-yl-pyridin-3-yl)-5-chloro-3,3-dimethyl-2,3-dihydro-isoindol-1-one hydrochloride (example 33[C]) (30 mg, 0.082 mmol) and DIEPA (50 mg, 0.39 mmol) in DCM (5 mL) at 0° C. was added 4-methylnicotinic acid (30 mg, 0.22 mmol) and HATU (50 mg, 0.13). After being stirred at 0° C. for 2 hours, the reaction solution was concentrated under reduced pressure. The residue was purified by prep-HPLC to give the title compound (10.8 mg) as a white solid. MS: 447.3 (M+H)+.

Example 37

5-Chloro-2-[5-(4-fluoro-1-propylsulfonyl-4-piperidyl)-3-pyridyl]-3,3-dimethyl-isoindolin-1-one

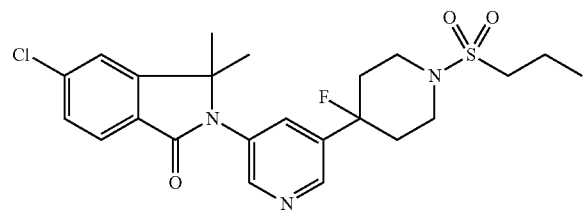 [SMILES: CCCS(=O)(=O)N1CCC(F)(c2cncc(N3C(=O)c4ccc(Cl)cc4C3(C)C)c2)CC1]

In analogy to the procedure described for the preparation of example 30[D], propane-1-sulfonyl chloride was used to yield the title compound (5 mg) as a white solid. MS: 480.1 (M+H)+.

Example 38

5-Chloro-2-[5-(1-cyclopropylsulfonyl-4-fluoro-4-piperidyl)-3-pyridyl]-3,3-dimethyl-isoindolin-1-one

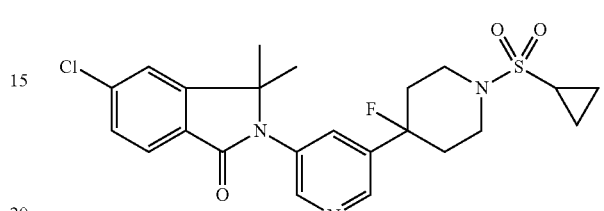

In analogy to the procedure described for the preparation of example 30[D], cyclopropanesulfonyl chloride was used to yield the title compound (6 mg) as a white solid. MS: 478.2 (M+H)+.

Example 39

2-[5-(4-Fluoro-1-isopropylsulfonyl-4-piperidyl)-3-pyridyl]-3,3-dimethyl-1-oxo-isoindoline-5-carbonitrile

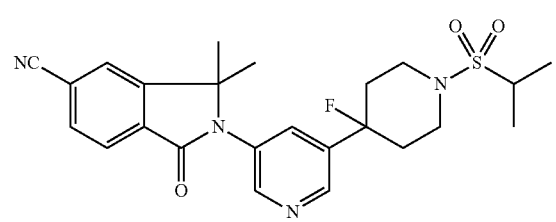 [SMILES: CC(C)S(=O)(=O)N1CCC(F)(c2cncc(N3C(=O)c4ccc(C#N)cc4C3(C)C)c2)CC1]

In analogy to the procedure described for the preparation of example 30, 3,3-dimethyl-1-oxo-2,3-dihydro-1H-isoindole-5-carbonitrile (step C) and propane-2-sulfonyl chloride (step D) were used to yield the title compound (5 mg) as a white solid. MS: 471.2 (M+H)+.

Example 40

6-[5-(1-Ethylsulfonyl-4-fluoro-4-piperidyl)-3-pyridyl]-2-methoxy-7,7-dimethyl-pyrrolo[3,4-b]pyridin-5-one

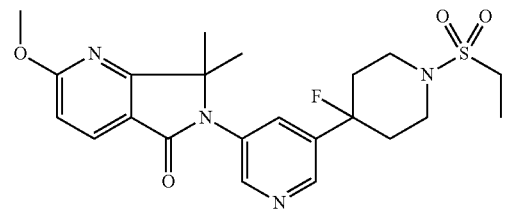 [SMILES: CCS(=O)(=O)N1CCC(F)(c2cncc(N3C(=O)c4ccc(OC)nc4C3(C)C)c2)CC1]

65

[A] tert-Butyl 4-fluoro-4-[5-(2-methoxy-7,7-dimethyl-5-oxo-pyrrolo[3,4-b]pyridin-6-yl)-3-pyridyl]piperidine-1-carboxylate

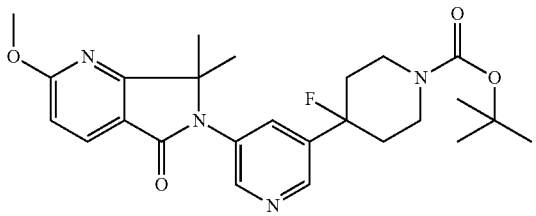 [SMILES: COc1ccc2c(n1)C(C)(C)N(c1cncc(C3(F)CCN(C(=O)OC(C)(C)C)CC3)c1)C2=O]

In analogy to the procedure described for the preparation of example 7[C], tert-butyl 4-(5-bromo-3-pyridyl)-4-fluoropiperidine-1-carboxylate and 2-methoxy-7,7-dimethyl-6H-pyrrolo[3,4-b]pyridine-5-one were used to yield the title compound as a crude product. It was used directly in the next step without further purification. MS: 471.1 (M+H)+.

[B] 6-[5-(1-Ethylsulfonyl-4-fluoro-4-piperidyl)-3-pyridyl]-2-methoxy-7,7-dimethyl-pyrrolo[3,4-b]pyridin-5-one

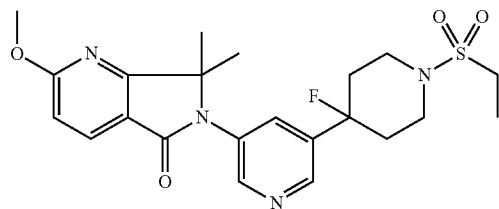 [SMILES: CCS(=O)(=O)N1CCC(F)(c2cncc(N3C(=O)c4ccc(OC)nc4C3(C)C)c2)CC1]

In analogy to the procedure described for the preparation of example 7[D], ethanesulfonyl chloride was used to yield the title compound (14 mg, 30%) as a white solid. MS: 463.1 (M+H)+.

66

Example 41

6-[5-[4-Fluoro-1-(1-methylpyrazole-4-carbonyl)-4-piperidyl]-3-pyridyl]-2-methoxy-7,7-dimethyl-pyrrolo[3,4-b]pyridin-5-one

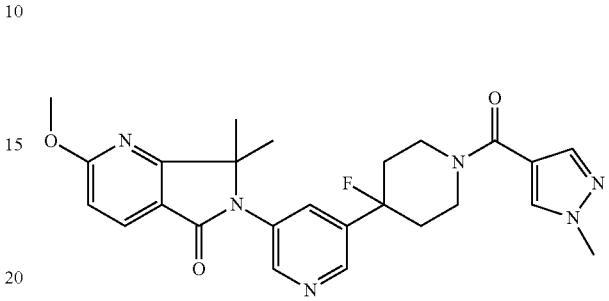

To a solution of tert-butyl 4-fluoro-4-[5-(2-methoxy-7,7-dimethyl-5-oxo-pyrrolo[3,4-b]pyridin-6-yl)-3-pyridyl]piperidine-1-carboxylate (47.0 mg, 0.1 mmol) (example 40 [A]) in MeOH (10 mL) was added AcCl (0.5 mL, 0.71 mmol) at 0° C. and the mixture was stirred at room temperature for 1 hour. The reaction solution was concentrated in vacuo to give a crude intermediate as yellowish oil (MS: 371.1 (M+H)+. It was dried under high vacuo for 2 hours before it was re-dissolved in 5 mL of DCM followed by the addition of DIEPA (0.5 mL), 1-methylpyrazole-4-carboxylic acid (28 mg, 0.22 mmol) and HATU (50 mg, 0.13) at 0° C. The resulting mixture was stirred at 0° C. for 2 hours and concentrated under reduced pressure. The residue was purified by prep-HPLC to give desired title compound (13 mg, 27%) as a white solid. MS: 479.1 (M+H)+.

The following examples listed in Table 2 were prepared in analogy to the procedures described for the preparation of examples 40 and 41 using appropriate starting materials:

TABLE 2

| Ex | Name | Reactant | MS (M + H+) |
|---|---|---|---|
| 42 | 6-[5-(4-Fluoro-1-isopropylsulfonyl-4-piperidyl)-3-pyridyl]-2-methoxy-7,7-dimethyl-pyrrolo[3,4-b]pyridin-5-one | 5-Bromo-4'-fluoro-3',4',5',6'-tetrahydro-2'H-[3,4']bipyridinyl-1'-carboxylic acid tert-butyl ester (Example 30[B]) and propane-2-sulfonyl chloride | 477.1 |

TABLE 2-continued

| Ex | Name | Reactant | MS (M + H+) |
|---|---|---|---|
| 43 | 6-[5-(4-Fluoro-1-propylsulfonyl-4-piperidyl)-3-pyridyl]-2-methoxy-7,7-dimethyl-pyrrolo[3,4-b]pyridin-5-one | 5-Bromo-4'-fluoro-3',4',5',6'-tetrahydro-2'H-[3,4']bipyridinyl-1'-carboxylic acid tert-butyl ester (Example 30[B]) and propane-1-sulfonyl chloride | 477.1 |
| 44 | 6-[5-(4-Fluoro-1-(1-methylimidazole-2-carbonyl)-4-piperidyl]-3-pyridyl]-2-methoxy-7,7-dimethyl-pyrrolo[3,4-b]pyridin-5-one | 5-Bromo-4'-fluoro-3',4',5',6'-tetrahydro-2'H-[3,4']bipyridinyl-1'-carboxylic acid tert-butyl ester (Example 30[B]) and 1-methylimidazole-2-carboxylic acid | 479.1 |
| 45 | 6-[5-(1-Cyclopropylsulfonyl-4-fluoro-4-piperidyl)-3-pyridyl]-2-methoxy-7,7-dimethyl-pyrrolo[3,4-b]pyridin-5-one | 5-Bromo-4'-fluoro-3',4',5',6'-tetrahydro-2'H-[3,4']bipyridinyl-1'-carboxylic acid tert-butyl ester (Example 30[B]) and cyclopropane-sulfonyl chloride | 475.1 |
| 46 | 6-[5-(1-Ethylsulfonyl-4-piperidyl)-3-pyridyl]-2-methoxy-7,7-dimethyl-pyrrolo[3,4-b]pyridin-5-one | 5-Iodo-3',4',5',6'-tetrahydro-2'H-[3,4']bipyridinyl-1'-carboxylic acid tert-butyl ester (Example 15[C]) and ethanesulfonyl chloride | 445.1 |
| 47 | 2-Methoxy-7,7-dimethyl-6-[5-[1-(1-methylpyrazole-4-carbonyl)-4-piperidyl]-3-pyridyl]pyrrolo[3,4-b]pyridin-5-one | 5-Iodo-3',4',5',6'-tetrahydro-2'H-[3,4']bipyridinyl-1'-carboxylic acid tert-butyl ester (Example 15[C]) and 1-methylpyrazole-4-carboxylic acid | 461.1 |

TABLE 2-continued

| Ex | Name | Reactant | MS (M + H⁺) |
|---|---|---|---|
| 48 | 2-Methoxy-7,7-dimethyl-6-[5-[1-(2-methylpyrazole-3-carbonyl)-4-piperidyl]-3-pyridyl]pyrrolo[3,4-b]pyridin-5-one | 5-Iodo-3',4',5',6'-tetrahydro-2'H-[3,4']bipyridinyl-1'-carboxylic acid tert-butyl ester (Example 15[C]) and 1-methylimidazole-2-carboxylic acid | 461.1 |
| 49 | 2-Methoxy-7,7-dimethyl-6-[5-[1-(4-methylpyridine-3-carbonyl)-4-piperidyl]-3-pyridyl]pyrrolo[3,4-b]pyridin-5-one | 5-Iodo-3',4',5',6'-tetrahydro-2'H-[3,4']bipyridinyl-1'-carboxylic acid tert-butyl ester (Example 15[C]) and 4-methylpyridine-3-carboxylic acid | 472.1 |

Example A

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A Compound of formula (I)

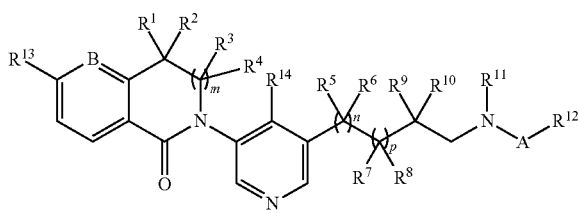

wherein
$R^1$, $R^2$, $R^3$ and $R^4$ are independently selected from H, alkyl and cycloalkyl;
$R^5$, $R^6$, $R^7$ and $R^9$ are independently selected from H, alkyl, halogen and hydroxy;
$R^8$ and $R^{11}$ together form —CH₂—CH₂—;
$R^{10}$ is H or $R^{10}$ and $R^{11}$ together form —(CH₂)$_w$—;
A is —C(O)— or —S(O)₂—;
B is —C— or —N—;
$R^{12}$ is alkyl, cycloalkyl or substituted heteroaryl, wherein substituted heteroaryl is substituted with one to three substituent independently selected from H, alkyl, cycloalkyl, hydroxy, alkoxy, cyano and halogen;
$R^{13}$ is halogen, cyano, alkoxy or haloalkoxy;
$R^{14}$ is H, alkyl or halogen;
m, n and p are independently selected from zero and 1;
w is 1, 2 or 3;
with the proviso that 2-[5-(1-acetyl-pyrrolidin-3-yl)-pyridin-3-yl]-5-chloro-3,3-dimethyl-2,3-dihydro-isoindol-1-one and 2-(1'-acetyl-1',2',3',4',5',6'-hexahydro-[3,4']bipyridinyl-5-yl)-5-chloro-3,3-dimethyl-2,3-dihydro-isoindol-1-one are excluded;

or a and pharmaceutically acceptable salt thereof.

2. The compound according to claim 1, wherein $R^1$ and $R^2$ are independently selected from H and alkyl.

3. The compound according to claim 1, wherein $R^1$ and $R^2$ are alkyl.

4. The compound according to claim 1, wherein $R^1$ and $R^2$ are methyl.

5. The compound according to claim 1, wherein m and n is zero.

6. The compound according to claim 1, wherein p is 1.

7. The compound according to claim 1 wherein $R^7$ is H or halogen.

8. The compound according to claim 1, wherein $R^7$ is H.

9. The compound according to claim 1, wherein $R^9$ is H.

10. The compound according to claim 1, wherein $R^{10}$ is H.

11. The compound according to claim 1, wherein A is —S(O)$_2$—.

12. The compound according to claim 1, wherein $R^{12}$ is alkyl or cycloalkyl.

13. The compound according to claim 1, wherein $R^{12}$ is alkyl.

14. The compound according to claim 1, wherein $R^{12}$ is ethyl, propyl, isopropyl.

15. The compound according to claim 1, wherein $R^{12}$ is ethyl.

16. The compound according to claim 1, wherein $R^{13}$ is chloro.

17. The compound according to claim 1, wherein $R^{14}$ is H.

18. The compound according to claim 1, wherein $R^1$ and $R^2$ are methyl, $R^7$, $R^9$, $R^{10}$ and $R^{14}$ are H, $R^{13}$ is chloro, A is —S(O)$_2$—, m and n are zero, p is 1 and $R^{12}$ is alkyl or cycloalkyl.

19. The compound according to claim 1, wherein $R^1$ and $R^2$ are methyl, $R^7$, $R^9$, $R^{10}$ and $R^{14}$ are H, $R^{13}$ is chloro, A is —S(O)$_2$—, m and n are zero, p is 1 and $R^{12}$ is alkyl.

20. The compound according to claim 1, selected from
5-Chloro-3,3-dimethyl-2-[5-(1-propanoylpiperidin-4-yl)pyridin-3-yl]isoindol-1-one;
5-Chloro-2-[5-(1-ethylsulfonylpiperidin-4-yl)pyridin-3-yl]-3,3-dimethylisoindol-1-one;
5-Chloro-3,3-dimethyl-2-[5-(1-methylsulfonylpiperidin-4-yl)pyridin-3-yl]isoindol-1-one;
5-Chloro-2-[5-(1-ethylsulfonylpiperidin-3-yl)pyridin-3-yl]-3,3-dimethylisoindol-1-one;
5-Chloro-3,3-dimethyl-2-[5-[(3R or 3S)-1-methylsulfonylpiperidin-3-yl]pyridin-3-yl]isoindol-1-one;
5-Chloro-3,3-dimethyl-2-[5-[(3S or 3R)-1-methylsulfonylpiperidin-3-yl]pyridin-3-yl]isoindol-1-one;
5-Chloro-2-[5-(1-ethylsulfonylpyrrolidin-3-yl)pyridin-3-yl]-3,3-dimethylisoindol-1-one;
5-Chloro-3,3-dimethyl-2-[5-[(3R or 3S)-1-propylsulfonylpyrrolidin-3-yl]pyridin-3-yl]isoindol-1-one;
5-Chloro-3,3-dimethyl-2-[5-[(3S or 3R)-1-propylsulfonylpyrrolidin-3-yl]pyridin-3-yl]isoindol-1-one;
5-Chloro-3,3-dimethyl-2-[5-[(3R or 3S)-1-propan-2-ylsulfonylpyrrolidin-3-yl]pyridin-3-yl]isoindol-1-one;
5-Chloro-3,3-dimethyl-2-[5-[(3S or 3R)-1-propan-2-ylsulfonylpyrrolidin-3-yl]pyridin-3-yl]isoindol-1-one;
5-Chloro-2-[5-[(3R or 3S)-1-cyclopropylsulfonylpyrrolidin-3-yl]pyridin-3-yl]-3,3-dimethylisoindol-1-one;
5-Chloro-2-[5-[(3S or 3R)-1-cyclopropylsulfonylpyrrolidin-3-yl]pyridin-3-yl]-3,3-dimethylisoindol-1-one;
5-Chloro-2-[5-(3-fluoro-1-propan-2-ylsulfonylpyrrolidin-3-yl)pyridin-3-yl]-3,3-dimethylisoindol-1-one;
5-Chloro-3,3-dimethyl-2-[5-(1-propylsulfonylpiperidin-4-yl)pyridin-3-yl]isoindol-1-one;
5-Chloro-3,3-dimethyl-2-[5-(1-propan-2-ylsulfonylpiperidin-4-yl)pyridin-3-yl]isoindol-1-one;
5-Chloro-2-[5-(1-cyclopropylsulfonylpiperidin-4-yl)pyridin-3-yl]-3,3-dimethylisoindol-1-one;
5-Chloro-3,3-dimethyl-2-[5-[1-(4-methylpyridine-3-carbonyl)piperidin-4-yl]pyridin-3-yl]isoindol-1-one;
5-Chloro-2-[5-[1-(3-chloropyridine-4-carbonyl)piperidin-4-yl]pyridin-3-yl]-3,3-dimethylisoindol-1-one;
5-Chloro-2-[5-[1-(3-chloropyridine-2-carbonyl)piperidin-4-yl]pyridin-3-yl]-3,3-dimethylisoindol-1-one;
5-Chloro-2-[5-(1-ethylsulfonylpiperidin-4-yl)pyridin-3-yl]-3H-isoindol-1-one;
5-Chloro-2-[5-(1-propan-2-ylsulfonylpiperidin-4-yl)pyridin-3-yl]-3H-isoindol-1-one;
5-Chloro-2-[5-[1-(4-methylpyridine-3-carbonyl)piperidin-4-yl]pyridin-3-yl]-3H-isoindol-1-one;
(3R or 3S)-5-Chloro-2-[5-(1-ethylsulfonylpiperidin-4-yl)pyridin-3-yl]-3-methyl-3H-isoindol-1-one;
(3S or 3R)-5-Chloro-2-[5-(1-ethylsulfonylpiperidin-4-yl)pyridin-3-yl]-3-methyl-3H-isoindol-1-one;
(3R or 3S)-5-Chloro-3-methyl-2-[5-(1-propan-2-ylsulfonylpiperidin-4-yl)pyridin-3-yl]-3H-isoindol-1-one;
(3S or 3R)-5-Chloro-3-methyl-2-[5-(1-propan-2-ylsulfonylpiperidin-4-yl)pyridin-3-yl]-3H-isoindol-1-one;
(3R or 3S)-5-Chloro-3-methyl-2-[5-[1-(4-methylpyridine-3-carbonyl)piperidin-4-yl]pyridin-3-yl]-3H-isoindol-1-one;
(3S or 3R)-5-Chloro-3-methyl-2-[5-[1-(4-methylpyridine-3-carbonyl)piperidin-4-yl]pyridin-3-yl]-3H-isoindol-1-one;
5-Chloro-2-[5-(1-ethylsulfonyl-4-fluoropiperidin-4-yl)pyridin-3-yl]-3,3-dimethylisoindol-1-one;
5-Chloro-2-[5-(4-fluoro-1-propan-2-ylsulfonylpiperidin-4-yl)pyridin-3-yl]-3,3-dimethylisoindol-1-one;
5-Chloro-2-[5-(1-ethylsulfonylazetidin-3-yl)pyridin-3-yl]-3,3-dimethylisoindol-1-one;
2-[5-(1-Acetylazetidin-3-yl)pyridin-3-yl]-5-chloro-3,3-dimethylisoindol-1-one;
5-Chloro-3,3-dimethyl-2-[5-(1-propylsulfonylazetidin-3-yl)pyridin-3-yl]isoindol-1-one;
5-Chloro-2-[5-(1-cyclopropylsulfonylazetidin-3-yl)pyridin-3-yl]-3,3-dimethylisoindol-1-one;
5-Chloro-3,3-dimethyl-2-[5-[1-(4-methylpyridine-3-carbonyl)azetidin-3-yl]pyridin-3-yl]isoindol-1-one;
5-Chloro-2-[5-(4-fluoro-1-propylsulfonyl-4-piperidyl)-3-pyridyl]-3,3-dimethyl-isoindolin-1-one;
5-Chloro-2-[5-(1-cyclopropylsulfonyl-4-fluoro-4-piperidyl)-3-pyridyl]-3,3-dimethyl-isoindolin-1-one;
2-[5-(4-Fluoro-1-isopropylsulfonyl-4-piperidyl)-3-pyridyl]-3,3-dimethyl-1-oxo-isoindoline-5-carbonitrile;
6-[5-(1-Ethylsulfonyl-4-fluoro-4-piperidyl)-3-pyridyl]-2-methoxy-7,7-dimethyl-pyrrolo[3,4-b]pyridin-5-one;
6-[5-[4-Fluoro-1-(1-methylpyrazole-4-carbonyl)-4-piperidyl]-3-pyridyl]-2-methoxy-7,7-dimethyl-pyrrolo[3,4-b]pyridin-5-one;
6-[5-(4-Fluoro-1-isopropylsulfonyl-4-piperidyl)-3-pyridyl]-2-methoxy-7,7-dimethyl-pyrrolo[3,4-b]pyridin-5-one;
6-[5-(4-Fluoro-1-propylsulfonyl-4-piperidyl)-3-pyridyl]-2-methoxy-7,7-dimethyl-pyrrolo[3,4-b]pyridin-5-one;
6-[5-[4-Fluoro-1-(1-methylimidazole-2-carbonyl)-4-piperidyl]-3-pyridyl]-2-methoxy-7,7-dimethyl-pyrrolo[3,4-b]pyridin-5-one;

6-[5-(1-Cyclopropylsulfonyl-4-fluoro-4-piperidyl)-3-pyridyl]-2-methoxy-7,7-dimethyl-pyrrolo[3,4-b]pyridin-5-one;

6-[5-(1-Ethylsulfonyl-4-piperidyl)-3-pyridyl]-2-methoxy-7,7-dimethyl-pyrrolo[3,4-b]pyridin-5-one;

2-Methoxy-7,7-dimethyl-6-[5-[1-(1-methylpyrazole-4-carbonyl)-4-piperidyl]-3-pyridyl]pyrrolo[3,4-b]pyridin-5-one;

2-Methoxy-7,7-dimethyl-6-[5-[1-(2-methylpyrazole-3-carbonyl)-4-piperidyl]-3-pyridyl]pyrrolo[3,4-b]pyridin-5-one;

2-Methoxy-7,7-dimethyl-6-[5-[1-(4-methylpyridine-3-carbonyl)-4-piperidyl]-3-pyridyl]pyrrolo[3,4-b]pyridin-5-one;

and pharmaceutically acceptable salts thereof.

21. The compound according to claim 1, selected from
5-Chloro-2-[5-(1-ethylsulfonylpiperidin-4-yl)pyridin-3-yl]-3,3-dimethylisoindol-1-one;
5-Chloro-3,3-dimethyl-2-[5-(1-propylsulfonylpiperidin-4-yl)pyridin-3-yl]isoindol-1-one;
5-Chloro-3,3-dimethyl-2-[5-(1-propan-2-ylsulfonylpiperidin-4-yl)pyridin-3-yl]isoindol-1-one;
5-Chloro-2-[5-(1-cyclopropylsulfonylpiperidin-4-yl)pyridin-3-yl]-3,3-dimethylisoindol-1-one;
(3R or 3S)-5-Chloro-2-[5-(1-ethylsulfonylpiperidin-4-yl)pyridin-3-yl]-3-methyl-3H-isoindol-1-one
5-Chloro-2-[5-(1-cyclopropylsulfonyl-4-fluoro-4-piperidyl)-3-pyridyl]-3,3-dimethyl-isoindolin-1-one;
2-[5-(4-Fluoro-1-isopropylsulfonyl-4-piperidyl)-3-pyridyl]-3,3-dimethyl-1-oxo-isoindoline-5-carbonitrile;

and pharmaceutically acceptable salts thereof.

22. The compound according to claim 1, wherein the compound is

5-Chloro-2-[5-(1-ethylsulfonylpiperidin-4-yl)pyridin-3-yl]-3,3-dimethylisoindol-1-one;

and pharmaceutically acceptable salts thereof.

23. A process to prepare a compound according to claim 1 comprising the reaction of a compound of formula (II) in the presence of a compound of formula (III);

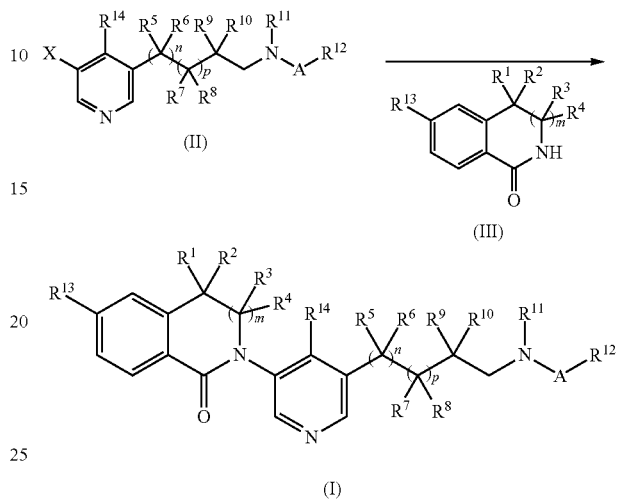

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, A, m, n and p are as defined in claim 1 and X is halogen or triflate.

24. A pharmaceutical composition comprising a compound according to claim 1 and a therapeutically inert carrier.

* * * * *